US012721993B2

(12) United States Patent
Merchant et al.

(10) Patent No.: US 12,721,993 B2
(45) Date of Patent: Sep. 1, 2026

(54) INTRAVASCULAR BLOOD PUMPS AND CONTROL THEREOF

(71) Applicant: SUPIRA MEDICAL, INC., Los Gatos, CA (US)

(72) Inventors: Adnan Merchant, Fremont, CA (US); Ari Ryan, San Jose, CA (US); Joshua Wallin, San Jose, CA (US); Gerald Lyons, Saratoga, CA (US); Daniel Varghai, Scotts Valley, CA (US)

(73) Assignee: Supira Medical, Inc., Los Gatos, CA (US)

( * ) Notice: Subject to any disclaimer, the term of this patent is extended or adjusted under 35 U.S.C. 154(b) by 859 days.

(21) Appl. No.: 17/997,489

(22) PCT Filed: Apr. 28, 2021

(86) PCT No.: PCT/US2021/029640
§ 371 (c)(1),
(2) Date: Oct. 28, 2022

(87) PCT Pub. No.: WO2021/222403
PCT Pub. Date: Nov. 4, 2021

(65) Prior Publication Data

US 2023/0166096 A1 Jun. 1, 2023

Related U.S. Application Data

(60) Provisional application No. 63/016,667, filed on Apr. 28, 2020.

(51) Int. Cl.
*A61M 60/538* (2021.01)
*A61M 60/13* (2021.01)
(Continued)

(52) U.S. Cl.
CPC .......... *A61M 60/13* (2021.01); *A61M 60/546* (2021.01); *A61M 60/554* (2021.01); *A61M 2205/18* (2013.01)

(58) Field of Classification Search
None
See application file for complete search history.

(56) References Cited

U.S. PATENT DOCUMENTS 1,061,107 A 5/1913 Nordmark
1,596,933 A 8/1926 Kister
(Continued)

FOREIGN PATENT DOCUMENTS

CA 2352234 A1 6/2000
CA 2739899 C 5/2017
(Continued)

OTHER PUBLICATIONS

Varghai et al.; U.S. Appl. No. 18/000,265 entitled "Intravascular blood pumps ," filed Nov. 29, 2022.
(Continued)

*Primary Examiner* — Shirley X Jian
(74) *Attorney, Agent, or Firm* — Shay Glenn LLP

(57) ABSTRACT

Intravascular blood pump systems that include a catheter assembly and an external console assembly. The catheter assembly may be in one or more of fluidic or electrical communication. The catheter assembly may include a controller with an executable method stored therein, wherein the executable method may be configured to receive sensed information that is indicative of a sensed characteristic of fluid in a fluid pathway, at least a portion of the fluid pathway disposed within the catheter assembly, and cause an alert if any of the sensed information is indicative that the external console assembly is not functioning properly.

20 Claims, 8 Drawing Sheets

(51) Int. Cl.
*A61M 60/546* (2021.01)
*A61M 60/554* (2021.01)

(56) References Cited

U.S. PATENT DOCUMENTS 3,152,618 A 10/1964 Rothermel et al.
3,175,555 A 3/1965 Ling
3,178,833 A 4/1965 Gulbransen, Jr.
3,208,448 A 9/1965 Woodward
3,233,609 A 2/1966 Leucci
3,421,497 A 1/1969 Chesnut
3,502,412 A 3/1970 Burns
3,504,662 A 4/1970 Jones
3,505,987 A 4/1970 Heilman
3,568,659 A 3/1971 Karnegis
3,693,612 A 9/1972 Donahoe et al.
3,734,648 A 5/1973 Nielson
3,774,243 A 11/1973 Ng et al.
3,837,922 A 9/1974 Ng et al.
3,841,837 A 10/1974 Kitrilakis et al.
3,860,968 A 1/1975 Shapiro
3,919,722 A 11/1975 Harmison
4,015,590 A 4/1977 Normann
4,037,984 A 7/1977 Rafferty et al.
4,046,137 A 9/1977 Curless et al.
4,058,857 A 11/1977 Runge et al.
4,093,726 A 6/1978 Winn et al.
4,135,253 A 1/1979 Reich et al.
4,142,845 A 3/1979 Lepp et al.
4,173,796 A 11/1979 Jarvik
4,190,047 A 2/1980 Jacobsen et al.
4,255,821 A 3/1981 Carol et al.
4,289,141 A 9/1981 Cormier
4,310,930 A 1/1982 Goldowsky
4,311,133 A 1/1982 Robinson
4,328,806 A 5/1982 Cooper
4,370,983 A 2/1983 Lichtenstein
4,381,005 A 4/1983 Bujan
4,381,567 A 5/1983 Robinson et al.
4,382,199 A 5/1983 Isaacson
4,389,737 A 6/1983 Robinson et al.
4,397,049 A 8/1983 Robinson et al.
4,407,304 A 10/1983 Lieber et al.
4,506,658 A 3/1985 Casile
4,515,589 A 5/1985 Austin et al.
4,522,195 A 6/1985 Schiff
4,524,466 A 6/1985 Hall et al.
4,551,073 A 11/1985 Schwab
4,576,606 A 3/1986 Pol et al.
4,585,004 A 4/1986 Brownlee
4,585,007 A 4/1986 Uchigaki et al.
4,599,081 A 7/1986 Cohen
4,600,405 A 7/1986 Zibelin
4,623,350 A 11/1986 Lapeyre et al.
4,625,712 A 12/1986 Wampler
4,652,265 A 3/1987 McDougall
4,662,358 A 5/1987 Farrar et al.
4,666,598 A 5/1987 Heath et al.
4,675,361 A 6/1987 Ward
4,685,910 A 8/1987 Schweizer
4,726,379 A 2/1988 Altman et al.
4,753,221 A 6/1988 Kensey et al.
4,767,289 A 8/1988 Parrott et al.
4,771,777 A 9/1988 Horzewski et al.
4,779,614 A 10/1988 Moise
4,782,817 A 11/1988 Singh et al.
4,785,795 A 11/1988 Singh
4,802,650 A 2/1989 Stricker
4,818,186 A 4/1989 Pastrone et al.
4,826,481 A 5/1989 Sacks et al.
4,846,152 A 7/1989 Wampler et al.
4,846,831 A 7/1989 Skillin
4,850,957 A 7/1989 Summers
4,888,009 A 12/1989 Lederman et al.
4,888,011 A 12/1989 Kung et al.
4,902,272 A 2/1990 Milder et al.
4,907,592 A 3/1990 Harper
4,908,012 A 3/1990 Moise et al.
4,919,647 A 4/1990 Nash
4,936,759 A 6/1990 Clausen et al.
4,961,738 A 10/1990 Mackin
4,976,683 A 12/1990 Gauthier et al.
4,995,857 A 2/1991 Arnold
5,026,367 A 6/1991 Leckrone et al.
D318,113 S 7/1991 Moutafis et al.
5,045,051 A 9/1991 Milder et al.
5,046,503 A 9/1991 Schneiderman
5,047,147 A 9/1991 Chevallet et al.
5,049,134 A 9/1991 Golding et al.
5,061,256 A 10/1991 Wampler
5,084,064 A 1/1992 Barak et al.
5,089,016 A 2/1992 Millner et al.
5,090,957 A 2/1992 Moutafis et al.
5,092,844 A 3/1992 Schwartz et al.
5,092,879 A 3/1992 Jarvik
5,112,200 A 5/1992 Isaacson et al.
5,112,292 A 5/1992 Hwang et al.
5,114,399 A 5/1992 Kovalcheck
5,116,305 A 5/1992 Milder et al.
5,139,517 A 8/1992 Corral
5,145,333 A 9/1992 Smith
5,147,281 A 9/1992 Thornton et al.
5,171,264 A 12/1992 Merrill
5,180,378 A 1/1993 Kung et al.
5,192,314 A 3/1993 Daskalakis
5,200,050 A 4/1993 Ivory et al.
5,205,721 A 4/1993 Isaacson
5,211,546 A 5/1993 Isaacson et al.
5,261,411 A 11/1993 Hughes
5,270,005 A 12/1993 Raible
5,287,858 A 2/1994 Hammerslag et al.
5,300,111 A 4/1994 Panton et al.
5,300,112 A 4/1994 Barr
5,314,418 A 5/1994 Takano et al.
5,322,413 A 6/1994 Vescovini et al.
5,326,344 A 7/1994 Bramm et al.
5,363,856 A 11/1994 Hughes et al.
5,397,349 A 3/1995 Kolff et al.
5,399,074 A 3/1995 Nose et al.
5,405,251 A 4/1995 Sipin
5,441,636 A 8/1995 Chevallet et al.
5,443,504 A 8/1995 Hill
5,486,192 A 1/1996 Walinsky et al.
5,487,727 A 1/1996 Snider et al.
5,507,629 A 4/1996 Jarvik
5,507,795 A 4/1996 Chiang et al.
5,510,267 A 4/1996 Marshall
5,512,042 A 4/1996 Montoya et al.
5,531,789 A 7/1996 Yamazaki et al.
5,628,731 A 5/1997 Dodge et al.
5,630,835 A 5/1997 Brownlee
5,643,172 A 7/1997 Kung et al.
5,643,215 A 7/1997 Fuhrman et al.
5,653,696 A 8/1997 Shiber
5,662,643 A 9/1997 Kung et al.
5,676,526 A 10/1997 Kuwana et al.
5,683,231 A 11/1997 Nakazawa et al.
5,702,365 A 12/1997 King
5,713,730 A 2/1998 Nose et al.
5,735,892 A 4/1998 Myers et al.
5,749,839 A 5/1998 Kovacs
5,749,855 A 5/1998 Reitan
5,751,125 A 5/1998 Weiss
5,759,148 A 6/1998 Sipin
5,766,207 A 6/1998 Potter et al.
5,776,096 A 7/1998 Fields
5,800,138 A 9/1998 Merce Vives
5,800,457 A 9/1998 Gelbfish
5,803,720 A 9/1998 Ohara et al.
5,814,076 A 9/1998 Brownlee
5,814,102 A 9/1998 Guldner et al.
5,851,174 A 12/1998 Jarvik et al.
5,888,241 A 3/1999 Jarvik
5,906,579 A 5/1999 Vander Salm et al.

(56) References Cited

U.S. PATENT DOCUMENTS 5,910,124 A 6/1999 Rubin
5,919,369 A 7/1999 Ash
5,941,813 A 8/1999 Sievers et al.
5,957,672 A 9/1999 Aber
5,964,694 A 10/1999 Siess et al.
5,984,893 A 11/1999 Ward
6,007,478 A 12/1999 Siess et al.
6,013,058 A 1/2000 Prosl et al.
6,022,363 A 2/2000 Walker et al.
6,030,336 A 2/2000 Franchi
6,042,347 A 3/2000 Scholl et al.
6,053,943 A 4/2000 Edwin et al.
6,066,085 A 5/2000 Heilman et al.
6,066,152 A 5/2000 Strauss et al.
6,068,588 A 5/2000 Goldowsky
6,071,093 A 6/2000 Hart
6,071,258 A 6/2000 Dalke et al.
6,082,105 A 7/2000 Miyata
6,101,406 A 8/2000 Hacker et al.
6,106,509 A 8/2000 Loubser
6,113,536 A 9/2000 Hosn et al.
6,117,130 A 9/2000 Kung
6,117,390 A 9/2000 Corey
6,120,537 A 9/2000 Wampler
6,123,659 A 9/2000 Le Blanc et al.
6,123,726 A 9/2000 Mori et al.
6,129,660 A 10/2000 Nakazeki et al.
6,136,025 A 10/2000 Barbut et al.
6,139,487 A 10/2000 Siess
6,142,752 A 11/2000 Akamatsu et al.
6,146,771 A 11/2000 Wirt et al.
6,149,683 A 11/2000 Lancisi et al.
6,152,704 A 11/2000 Aboul-Hosn et al.
6,155,969 A 12/2000 Schima et al.
6,176,848 B1 1/2001 Rau et al.
6,180,058 B1 1/2001 Lindsay
6,197,055 B1 3/2001 Matthews
6,197,289 B1 3/2001 Wirt et al.
6,210,133 B1 4/2001 Hosn et al.
6,210,318 B1 4/2001 Lederman
6,228,023 B1 5/2001 Zaslavsky et al.
6,236,883 B1 5/2001 Ciaccio et al.
6,254,359 B1 7/2001 Aber
6,270,831 B2 8/2001 Kumar et al.
6,273,861 B1 8/2001 Bates et al.
6,283,949 B1 9/2001 Roorda
6,287,319 B1 9/2001 Aboul-Hosn et al.
6,290,685 B1 9/2001 Insley et al.
6,312,462 B1 11/2001 McDermott et al.
6,314,322 B1 11/2001 Rosenberg
6,319,231 B1 11/2001 Andrulitis
6,361,292 B1 3/2002 Chang et al.
6,361,501 B1 3/2002 Amano et al.
6,364,833 B1 4/2002 Valerio et al.
6,398,715 B1 6/2002 Magovern et al.
6,400,991 B1 6/2002 Kung
6,406,267 B1 6/2002 Mondiere
6,406,422 B1 6/2002 Landesberg
6,419,657 B1 7/2002 Pacetti
6,422,990 B1 7/2002 Prem
6,432,136 B1 8/2002 Weiss et al.
6,443,944 B1 9/2002 Doshi et al.
6,443,983 B1 9/2002 Nagyszalanczy et al.
6,445,956 B1 9/2002 Laird et al.
6,447,265 B1 9/2002 Antaki et al.
6,447,266 B2 9/2002 Antaki et al.
6,447,441 B1 9/2002 Yu et al.
6,497,680 B1 12/2002 Holst et al.
6,503,224 B1 1/2003 Forman et al.
6,503,450 B1 1/2003 Afzal et al.
6,508,787 B2 1/2003 Erbel et al.
6,508,806 B1 1/2003 Hoste
6,527,699 B1 3/2003 Goldowsky
6,533,716 B1 3/2003 Schmitz-Rode et al.
6,533,724 B2 3/2003 McNair
6,537,315 B2 3/2003 Yamazaki et al.
6,540,658 B1 4/2003 Fasciano et al.
6,540,659 B1 4/2003 Milbocker
6,544,543 B1 4/2003 Mandrusov et al.
6,547,716 B1 4/2003 Milbocker
6,562,022 B2 5/2003 Hoste et al.
6,572,529 B2 6/2003 Wilk
6,572,534 B1 6/2003 Milbocker et al.
6,595,943 B1 7/2003 Burbank
6,602,182 B1 8/2003 Milbocker
6,616,596 B1 9/2003 Milbocker
6,620,120 B2 9/2003 Landry et al.
6,623,420 B2 9/2003 Reich et al.
6,626,821 B1 9/2003 Kung et al.
6,626,889 B1 9/2003 Simpson et al.
6,626,935 B1 9/2003 Ainsworth et al.
6,632,215 B1 10/2003 Lemelson
6,635,083 B1 10/2003 Cheng et al.
6,656,220 B1 12/2003 Gomez et al.
6,669,624 B2 12/2003 Frazier
6,669,662 B1 12/2003 Webler
6,676,679 B1 1/2004 Mueller et al.
6,685,696 B2 2/2004 Fleischhacker et al.
6,688,869 B1 2/2004 Simonds
6,699,231 B1 3/2004 Sterman et al.
6,709,382 B1 3/2004 Homer
6,712,844 B2 3/2004 Pacetti
6,730,102 B1 5/2004 Burdulis et al.
6,746,416 B2 6/2004 Hubbard et al.
6,749,615 B2 6/2004 Burdulis et al.
6,769,871 B2 8/2004 Yamazaki
6,790,171 B1 9/2004 Gründeman et al.
6,811,749 B2 11/2004 Lindsay
6,821,295 B1 11/2004 Farrar
6,837,890 B1 1/2005 Chludzinski et al.
6,846,296 B1 1/2005 Milbocker et al.
6,866,650 B2 3/2005 Stevens et al.
6,879,126 B2 4/2005 Paden et al.
6,884,210 B2 4/2005 Nose et al.
6,908,280 B2 6/2005 Yamazaki
6,908,435 B1 6/2005 Mueller et al.
6,929,632 B2 8/2005 Nita et al.
6,929,660 B1 8/2005 Ainsworth et al.
6,942,672 B2 9/2005 Heilman et al.
6,945,978 B1 9/2005 Hyde
6,949,066 B2 9/2005 Beamson et al.
6,969,345 B2 11/2005 Jassawalla et al.
6,981,942 B2 1/2006 Khaw et al.
7,022,100 B1 4/2006 Hosn et al.
7,025,742 B2 4/2006 Rubenstein et al.
7,027,875 B2 4/2006 Siess et al.
7,029,483 B2 4/2006 Schwartz
7,037,253 B2 5/2006 French et al.
7,048,747 B2 5/2006 Arcia et al.
7,074,018 B2 7/2006 Chang
7,108,652 B2 9/2006 Stenberg et al.
7,118,525 B2 10/2006 Coleman et al.
7,122,151 B2 10/2006 Reeder et al.
7,125,376 B2 10/2006 Viole et al.
7,126,310 B1 10/2006 Barron
7,150,711 B2 12/2006 Nüsser et al.
7,155,291 B2 12/2006 Zarinetchi et al.
7,172,551 B2 2/2007 Leasure
7,189,260 B2 3/2007 Horvath et al.
7,220,275 B2 5/2007 Davidson et al.
7,229,258 B2 6/2007 Wood et al.
7,229,402 B2 6/2007 Diaz et al.
7,238,151 B2 7/2007 Frazier
7,244,224 B2 7/2007 Tsukahara et al.
7,247,166 B2 7/2007 Pienknagura
7,303,581 B2 12/2007 Peralta
7,331,972 B1 2/2008 Cox
7,331,987 B1 2/2008 Cox
7,361,726 B2 4/2008 Pacetti et al.
7,377,927 B2 5/2008 Burdulis et al.
7,392,077 B2 6/2008 Mueller et al.
7,393,181 B2 7/2008 McBride et al.
7,396,327 B2 7/2008 Morello
7,479,102 B2 1/2009 Jarvik

(56) References Cited

U.S. PATENT DOCUMENTS 7,520,850 B2 4/2009 Brockway
7,524,277 B1 4/2009 Wang et al.
7,541,000 B2 6/2009 Stringer et al.
7,544,160 B2 6/2009 Gross
7,547,391 B2 6/2009 Petrie
7,585,322 B2 9/2009 Azzolina
7,588,530 B2 9/2009 Heilman et al.
7,588,549 B2 9/2009 Eccleston
7,591,199 B2 9/2009 Weldon et al.
7,611,478 B2 11/2009 Lucke et al.
7,628,756 B2 12/2009 Hacker et al.
7,713,259 B2 5/2010 Gosiengfiao et al.
RE41,394 E 6/2010 Bugge et al.
7,731,664 B1 6/2010 Millar
7,736,296 B2 6/2010 Siess et al.
7,736,375 B2 6/2010 Crow
7,758,492 B2 7/2010 Weatherbee
7,776,991 B2 8/2010 Pacetti et al.
7,780,628 B1 8/2010 Keren et al.
7,794,419 B2 9/2010 Paolini et al.
7,794,743 B2 9/2010 Simhambhatla et al.
7,819,834 B2 10/2010 Paul
7,828,710 B2 11/2010 Shifflette
7,833,239 B2 11/2010 Nash
7,841,976 B2 11/2010 McBride et al.
7,850,594 B2 12/2010 Sutton et al.
7,862,501 B2 1/2011 Woodard
7,878,967 B1 2/2011 Khanal
7,914,436 B1 3/2011 Kung
7,922,657 B2 4/2011 Gillinov et al.
7,942,804 B2 5/2011 Khaw
7,963,905 B2 6/2011 Salmonsen et al.
7,972,122 B2 7/2011 LaRose et al.
7,972,291 B2 7/2011 Ibragimov
7,985,442 B2 7/2011 Gong
7,988,728 B2 8/2011 Ayre
7,993,259 B2 8/2011 Kang et al.
7,993,260 B2 8/2011 Bolling
7,993,358 B2 8/2011 O'Brien
7,998,054 B2 8/2011 Bolling
7,998,190 B2 8/2011 Gharib et al.
8,012,079 B2 9/2011 Delgado
8,012,194 B2 9/2011 Edwin et al.
8,012,508 B2 9/2011 Ludwig
8,029,728 B2 10/2011 Lindsay
8,034,098 B1 10/2011 Callas et al.
8,048,442 B1 11/2011 Hossainy et al.
8,052,749 B2 11/2011 Salahieh et al.
8,070,742 B2 12/2011 Woo
8,070,804 B2 12/2011 Hyde et al.
8,075,472 B2 12/2011 Zilbershlag et al.
8,079,948 B2 12/2011 Shifflette
8,083,726 B1 12/2011 Wang
8,123,669 B2 2/2012 Siess et al.
8,123,674 B2 2/2012 Kuyava
8,133,272 B2 3/2012 Hyde
RE43,299 E 4/2012 Siess
8,152,035 B2 4/2012 Eart
8,152,845 B2 4/2012 Bourque
8,153,083 B2 4/2012 Briggs
8,157,719 B1 4/2012 Ainsworth et al.
8,157,721 B2 4/2012 Sugiura
8,157,758 B2 4/2012 Pecor et al.
8,158,062 B2 4/2012 Dykes et al.
8,162,021 B2 4/2012 Tomasetti et al.
8,167,589 B2 5/2012 Hidaka et al.
8,172,783 B1 5/2012 Ray
8,177,750 B2 5/2012 Steinbach et al.
8,187,324 B2 5/2012 Webler et al.
8,197,463 B2 6/2012 Intoccia
8,210,829 B2 7/2012 Horvath et al.
8,241,199 B2 8/2012 Maschke
8,257,258 B2 9/2012 Zocchi
8,257,375 B2 9/2012 Maschke
8,266,943 B2 9/2012 Miyakoshi et al.
D669,585 S 10/2012 Bourque
8,277,476 B2 10/2012 Taylor et al.
8,282,359 B2 10/2012 Ayre et al.
8,292,908 B2 10/2012 Nieman et al.
D671,646 S 11/2012 Bourque et al.
8,303,482 B2 11/2012 Schima et al.
8,323,173 B2 12/2012 Benkowski et al.
8,323,203 B2 12/2012 Thornton
8,328,750 B2 12/2012 Peters et al.
8,329,114 B2 12/2012 Temple
8,329,158 B2 12/2012 Hossainy et al.
8,366,599 B2 2/2013 Tansley et al.
8,372,137 B2 2/2013 Pienknagura
8,377,033 B2 2/2013 Basu et al.
8,377,083 B2 2/2013 Mauch et al.
8,382,695 B1 2/2013 Patel
8,388,565 B2 3/2013 Shifflette
8,388,649 B2 3/2013 Woodard et al.
8,419,609 B2 4/2013 Shambaugh et al.
8,419,944 B2 4/2013 Alkanhal
8,439,909 B2 5/2013 Wang et al.
8,449,444 B2 5/2013 Poirier
8,454,683 B2 6/2013 Rafiee et al.
8,485,961 B2 7/2013 Campbell et al.
8,496,874 B2 7/2013 Gellman et al.
8,500,620 B2 8/2013 Lu et al.
8,506,471 B2 8/2013 Bourque
8,535,211 B2 9/2013 Campbell et al.
8,535,212 B2 9/2013 Robert
8,538,515 B2 9/2013 Atanasoska et al.
8,545,382 B2 10/2013 Suzuki et al.
8,545,447 B2 10/2013 Demarais et al.
8,562,509 B2 10/2013 Bates
8,568,289 B2 10/2013 Mazur
8,579,858 B2 11/2013 Reitan et al.
8,579,967 B2 11/2013 Webler et al.
8,585,572 B2 11/2013 Mehmanesh
8,586,527 B2 11/2013 Singh
8,591,393 B2 11/2013 Walters et al.
8,591,394 B2 11/2013 Peters et al.
8,591,449 B2 11/2013 Hudson
8,591,538 B2 11/2013 Gellman
8,591,539 B2 11/2013 Gellman
D696,769 S 12/2013 Schenck et al.
8,597,170 B2 12/2013 Walters et al.
8,608,661 B1 12/2013 Mandrusov et al.
8,613,777 B2 12/2013 Siess et al.
8,613,892 B2 12/2013 Stafford
8,617,239 B2 12/2013 Reitan
8,631,680 B2 1/2014 Fleischli et al.
8,632,449 B2 1/2014 Masuzawa et al.
8,641,594 B2 2/2014 LaRose et al.
8,657,871 B2 2/2014 Limon
8,657,875 B2 2/2014 Kung et al.
8,668,473 B2 3/2014 LaRose et al.
8,684,903 B2 4/2014 Nour
8,690,749 B1 4/2014 Nunez
8,690,823 B2 4/2014 Yribarren et al.
8,697,058 B2 4/2014 Basu et al.
8,708,948 B2 4/2014 Consigny et al.
8,715,151 B2 5/2014 Poirier
8,715,156 B2 5/2014 Jayaraman
8,715,707 B2 5/2014 Hossainy et al.
8,721,516 B2 5/2014 Scheckel
8,721,517 B2 5/2014 Zeng et al.
8,734,331 B2 5/2014 Evans et al.
8,734,508 B2 5/2014 Hastings et al.
8,739,727 B2 6/2014 Austin et al.
8,740,920 B2 6/2014 Goldfarb et al.
8,741,287 B2 6/2014 Brophy et al.
8,758,388 B2 6/2014 Pah
8,766,788 B2 7/2014 D'Ambrosio
8,777,832 B1 7/2014 Wang et al.
8,790,399 B2 7/2014 Frazier et al.
8,795,576 B2 8/2014 Tao et al.
8,814,543 B2 8/2014 Liebing
8,814,776 B2 8/2014 Hastie et al.
8,814,933 B2 8/2014 Siess
8,815,274 B2 8/2014 DesNoyer et al.

(56) References Cited

U.S. PATENT DOCUMENTS 8,821,366 B2 9/2014 Farnan et al.
8,837,096 B2 9/2014 Seebruch
8,840,539 B2 9/2014 Zilbershlag
8,840,566 B2 9/2014 Seibel et al.
8,849,398 B2 9/2014 Evans
8,862,232 B2 10/2014 Zarinetchi et al.
8,864,642 B2 10/2014 Scheckel
8,876,685 B2 11/2014 Crosby et al.
8,882,744 B2 11/2014 Dormanen et al.
8,888,675 B2 11/2014 Stankus et al.
8,894,387 B2 11/2014 White
8,894,561 B2 11/2014 Callaway et al.
8,897,873 B2 11/2014 Schima et al.
8,900,060 B2 12/2014 Liebing
8,905,910 B2 12/2014 Reichenbach et al.
8,927,700 B2 1/2015 McCauley et al.
8,932,141 B2 1/2015 Liebing
8,932,197 B2 1/2015 Gregoric et al.
8,934,956 B2 1/2015 Glenn et al.
8,942,828 B1 1/2015 Schecter
8,944,748 B2 2/2015 Liebing
8,945,114 B2 * 2/2015 Elmouelhi ......... A61B 18/1477 606/41
8,945,159 B2 2/2015 Nussbaum
8,956,402 B2 2/2015 Cohn
8,961,387 B2 2/2015 Duncan
8,961,466 B2 2/2015 Steinbach
8,971,980 B2 3/2015 Mace et al.
8,974,519 B2 3/2015 Gennrich et al.
8,992,406 B2 3/2015 Corbett
8,997,349 B2 4/2015 Mori et al.
9,002,468 B2 4/2015 Shea et al.
9,023,010 B2 5/2015 Chiu et al.
9,028,216 B2 5/2015 Schumacher et al.
9,028,392 B2 5/2015 Shifflette
9,028,859 B2 5/2015 Hossainy et al.
9,033,863 B2 5/2015 Jarvik
9,033,909 B2 5/2015 Aihara
9,039,595 B2 5/2015 Ayre et al.
9,044,236 B2 6/2015 Nguyen et al.
9,056,159 B2 6/2015 Medvedev et al.
9,066,992 B2 6/2015 Stankus et al.
9,067,005 B2 6/2015 Ozaki et al.
9,067,006 B2 6/2015 Toellner
9,072,825 B2 7/2015 Pfeffer et al.
9,078,692 B2 7/2015 Shturman et al.
9,089,329 B2 7/2015 Hoarau et al.
9,089,634 B2 7/2015 Schumacher et al.
9,089,635 B2 7/2015 Reichenbach et al.
9,089,670 B2 7/2015 Scheckel
9,095,428 B2 8/2015 Kabir et al.
9,096,703 B2 8/2015 Li et al.
9,101,302 B2 8/2015 Mace et al.
9,125,977 B2 9/2015 Nishimura et al.
9,127,680 B2 9/2015 Yanal et al.
9,138,516 B2 9/2015 Vischer et al.
9,138,518 B2 9/2015 Campbell et al.
9,144,638 B2 9/2015 Zimmermann et al.
9,162,017 B2 10/2015 Evans et al.
9,168,361 B2 10/2015 Ehrenreich et al.
9,180,227 B2 11/2015 Ludwig et al.
9,180,235 B2 11/2015 Forsell
9,192,705 B2 11/2015 Yanai et al.
9,199,020 B2 12/2015 Siess
9,217,442 B2 12/2015 Wiessler et al.
D746,975 S 1/2016 Schenck et al.
9,227,002 B1 1/2016 Giridharan et al.
9,239,049 B2 1/2016 Jarnagin et al.
9,265,870 B2 2/2016 Reichenbach et al.
9,278,189 B2 3/2016 Corbett
9,283,314 B2 3/2016 Prasad et al.
9,291,591 B2 3/2016 Simmons et al.
9,295,550 B2 3/2016 Nguyen et al.
9,295,767 B2 3/2016 Schmid et al.
9,308,302 B2 4/2016 Zeng
9,308,304 B2 4/2016 Peters et al.
9,314,558 B2 4/2016 Er
9,314,559 B2 4/2016 Smith et al.
9,328,741 B2 5/2016 Liebing
9,333,284 B2 5/2016 Thompson et al.
9,339,596 B2 5/2016 Roehn
9,345,824 B2 5/2016 Mohl et al.
9,358,329 B2 6/2016 Fitzgerald et al.
9,358,330 B2 6/2016 Schumacher
9,364,255 B2 6/2016 Weber
9,364,592 B2 6/2016 McBride et al.
9,370,613 B2 6/2016 Hsu et al.
9,375,445 B2 6/2016 Hossainy et al.
9,381,285 B2 7/2016 Ozaki et al.
9,387,284 B2 7/2016 Heilman et al.
9,409,012 B2 8/2016 Eidenschink et al.
9,416,783 B2 8/2016 Schumacher et al.
9,416,791 B2 8/2016 Toellner
9,421,311 B2 8/2016 Tanner et al.
9,433,713 B2 9/2016 Corbett et al.
9,435,450 B2 9/2016 Muennich
9,446,179 B2 9/2016 Keenan et al.
9,452,249 B2 9/2016 Kearsley et al.
9,474,840 B2 10/2016 Siess
9,486,565 B2 11/2016 Göllner et al.
9,492,601 B2 11/2016 Casas et al.
9,504,491 B2 11/2016 Callas et al.
9,511,179 B2 12/2016 Casas et al.
9,512,839 B2 12/2016 Liebing
9,522,257 B2 12/2016 Webler
9,526,818 B2 12/2016 Kearsley et al.
9,533,084 B2 1/2017 Siess et al.
9,533,085 B2 1/2017 Hanna
9,539,378 B2 1/2017 Tuseth
9,550,017 B2 1/2017 Spanier et al.
9,555,173 B2 1/2017 Spanier
9,555,175 B2 1/2017 Bulent et al.
9,555,177 B2 1/2017 Curtis et al.
9,556,873 B2 1/2017 Yanal et al.
9,561,309 B2 2/2017 Glauser et al.
9,561,313 B2 2/2017 Taskin
9,592,328 B2 3/2017 Jeevanandam et al.
9,603,983 B2 3/2017 Roehn et al.
9,603,984 B2 3/2017 Romero et al.
9,611,743 B2 4/2017 Toeliner et al.
9,612,182 B2 * 4/2017 Olde .................. A61M 1/3661
9,616,157 B2 4/2017 Akdis
9,616,159 B2 4/2017 Anderson et al.
9,623,163 B1 4/2017 Fischi
9,631,754 B2 4/2017 Richardson et al.
9,642,984 B2 5/2017 Schumacher et al.
9,656,010 B2 5/2017 Burke
9,656,030 B1 5/2017 Webler et al.
9,662,211 B2 5/2017 Hodson et al.
9,669,141 B2 6/2017 Parker et al.
9,669,142 B2 6/2017 Spanier et al.
9,669,143 B2 6/2017 Guerrero
9,675,450 B2 6/2017 Straka et al.
9,675,738 B2 6/2017 Tanner et al.
9,675,739 B2 6/2017 Tanner et al.
9,675,742 B2 6/2017 Casas et al.
9,687,596 B2 6/2017 Poirier
9,687,630 B2 6/2017 Basu et al.
9,700,659 B2 7/2017 Kantrowitz et al.
9,713,662 B2 7/2017 Rosenberg et al.
9,713,663 B2 7/2017 Medvedev et al.
9,715,839 B2 7/2017 Pybus et al.
9,717,615 B2 8/2017 Grandt
9,717,832 B2 8/2017 Taskin et al.
9,717,839 B2 8/2017 Hashimoto
9,726,195 B2 8/2017 Cecere et al.
9,731,058 B2 8/2017 Siebenhaar et al.
9,731,101 B2 8/2017 Bertrand et al.
9,737,361 B2 8/2017 Magana et al.
9,737,651 B2 8/2017 Wampler
9,744,280 B2 8/2017 Schade et al.
9,744,287 B2 8/2017 Bulent et al.
9,750,859 B2 9/2017 Bulent et al.
9,757,502 B2 9/2017 Burke et al.

(56) References Cited

U.S. PATENT DOCUMENTS 9,770,202 B2 9/2017 Ralston et al.
9,770,543 B2 9/2017 Tanner et al.
9,771,801 B2 9/2017 Schumacher et al.
9,775,930 B2 10/2017 Michal et al.
9,782,279 B2 10/2017 Kassab
9,782,527 B2 10/2017 Thomas et al.
9,795,780 B2 10/2017 Serna et al.
9,801,987 B2 10/2017 Faman et al.
9,801,992 B2 10/2017 Giordano et al.
9,821,098 B2 11/2017 Horvath et al.
9,821,146 B2 11/2017 Tao et al.
9,827,356 B2 11/2017 Muller et al.
9,833,314 B2 12/2017 Corbett
9,833,550 B2 12/2017 Siess
9,833,551 B2 12/2017 Criscione et al.
9,839,734 B1 12/2017 Menon et al.
9,844,618 B2 12/2017 Muller-Spanka et al.
9,850,906 B2 12/2017 Ozaki et al.
9,855,437 B2 1/2018 Nguyen et al.
9,861,504 B2 1/2018 Abunassar et al.
9,861,731 B2 1/2018 Tamburino
9,872,948 B2 1/2018 Siess
9,878,087 B2 1/2018 Richardson et al.
9,878,169 B2 1/2018 Hossainy
9,889,242 B2 2/2018 Pfeffer et al.
9,895,244 B2 2/2018 Papp et al.
9,895,475 B2 2/2018 Toellner et al.
9,907,890 B2 3/2018 Muller
9,907,892 B2 3/2018 Broen et al.
9,913,937 B2 3/2018 Schwammenthal et al.
9,918,822 B2 3/2018 Abunassar et al.
9,919,085 B2 3/2018 Throckmorton et al.
9,919,088 B2 3/2018 Bonde et al.
9,919,089 B2 3/2018 Garrigue
9,950,101 B2 4/2018 Smith et al.
9,956,410 B2 5/2018 Deem et al.
9,962,258 B2 5/2018 Seguin et al.
9,974,893 B2 5/2018 Toellner
9,974,894 B2 5/2018 Morello
9,981,078 B2 5/2018 Jin et al.
9,985,374 B2 5/2018 Hodges
9,987,407 B2 6/2018 Grant et al.
10,010,273 B2 7/2018 Sloan et al.
10,022,499 B2 7/2018 Galasso
10,028,835 B2 7/2018 Kermode et al.
10,029,037 B2 7/2018 Muller et al.
10,029,038 B2 7/2018 Hodges
10,029,039 B2 7/2018 Dague et al.
10,031,124 B2 7/2018 Galasso
10,034,972 B2 7/2018 Wampler et al.
10,039,873 B2 8/2018 Siegenthaler
10,046,146 B2 8/2018 Manderfeld et al.
10,052,419 B2 8/2018 Er
10,058,349 B2 8/2018 Gunderson et al.
10,058,641 B2 8/2018 Mollison et al.
10,058,652 B2 8/2018 Tsoukalis
10,058,653 B2 8/2018 Wang et al.
10,077,777 B2 9/2018 Horvath et al.
10,080,828 B2 9/2018 Wiesener et al.
10,080,834 B2 9/2018 Federspiel et al.
10,080,871 B2 9/2018 Schumacher et al.
10,208,763 B2 2/2019 Schumacher et al.
10,357,598 B2 7/2019 Aboul-Hosn et al.
10,569,005 B2 2/2020 Solem et al.
10,583,231 B2* 3/2020 Schwammenthal ........................ A61B 17/12168
10,722,631 B2 7/2020 Salahieh et al.
10,881,770 B2 1/2021 Tuval et al.
10,894,115 B2 1/2021 Pfeffer et al.
11,033,681 B2* 6/2021 Eitan ................ A61M 5/16877
11,033,728 B2* 6/2021 Schenck ............. A61M 1/1524
11,123,538 B2 9/2021 Epple et al.
11,185,677 B2 11/2021 Salahieh et al.
11,229,784 B2 1/2022 Salahieh et al.
11,268,521 B2 3/2022 Toellner
11,280,345 B2 3/2022 Bredenbreuker et al.
11,511,103 B2 11/2022 Salahieh et al.
11,724,089 B2* 8/2023 Wallin ................ A61M 1/3639 600/17
11,850,413 B2 12/2023 Zeng et al.
12,017,056 B2 6/2024 Guo et al.
12,440,615 B1* 10/2025 Huszar ................... A61M 1/60
2001/0003802 A1 6/2001 Vitale
2001/0023369 A1 9/2001 Chobotov
2001/0046380 A1 11/2001 LeFebvre
2001/0053928 A1 12/2001 Edelman et al.
2002/0057989 A1 5/2002 Afzal et al.
2002/0058971 A1 5/2002 Zarinetchi et al.
2002/0068848 A1 6/2002 Zadini et al.
2002/0072679 A1 6/2002 Schock et al.
2002/0072779 A1 6/2002 Loeb
2002/0128709 A1 9/2002 Pless
2002/0147495 A1 10/2002 Petroff
2003/0069465 A1 4/2003 Benkowski et al.
2003/0088151 A1 5/2003 Kung et al.
2003/0131995 A1 7/2003 de Rouffignac et al.
2003/0155111 A1 8/2003 Vinegar et al.
2003/0173081 A1 9/2003 Vinegar et al.
2003/0173082 A1 9/2003 Vinegar et al.
2003/0173085 A1 9/2003 Vinegar et al.
2003/0178191 A1 9/2003 Maher et al.
2003/0209348 A1 11/2003 Ward et al.
2003/0217957 A1 11/2003 Bowman et al.
2004/0024285 A1 2/2004 Muckter
2004/0040715 A1 3/2004 Wellington et al.
2004/0097782 A1 5/2004 Korakianitis et al.
2004/0097783 A1 5/2004 Peters et al.
2004/0228724 A1 11/2004 Capone et al.
2004/0249363 A1 12/2004 Burke et al.
2005/0010077 A1 1/2005 Calderon
2005/0043805 A1 2/2005 Chudik
2005/0049696 A1 3/2005 Siess et al.
2005/0060036 A1 3/2005 Schultz et al.
2005/0113632 A1 5/2005 Ortiz et al.
2005/0119599 A1 6/2005 Kanz et al.
2005/0187616 A1 8/2005 Realyvasquez
2005/0209617 A1 9/2005 Koven et al.
2005/0220636 A1 10/2005 Henein et al.
2005/0246010 A1 11/2005 Alexander et al.
2005/0254976 A1 11/2005 Carrier et al.
2005/0256540 A1 11/2005 Silver et al.
2005/0277803 A1 12/2005 Pecor
2006/0111641 A1 5/2006 Manera et al.
2006/0116700 A1 6/2006 Crow
2006/0129082 A1 6/2006 Rozga
2006/0155158 A1 7/2006 Hosn
2006/0177343 A1 8/2006 Brian et al.
2006/0195098 A1 8/2006 Schumacher
2006/0257355 A1 11/2006 Stewart et al.
2006/0293664 A1 12/2006 Schumacher
2007/0106274 A1 5/2007 Ayre et al.
2007/0167091 A1 7/2007 Schumacher
2007/0203453 A1 8/2007 Mori et al.
2007/0213690 A1 9/2007 Phillips et al.
2007/0250148 A1 10/2007 Perry et al.
2007/0253842 A1 11/2007 Horvath et al.
2007/0265673 A1 11/2007 Ransbury et al.
2007/0270633 A1 11/2007 Cook et al.
2007/0299314 A1 12/2007 Bertolero et al.
2008/0045779 A1 2/2008 Rinaldi et al.
2008/0065014 A1 3/2008 Von Oepen et al.
2008/0076101 A1 3/2008 Hyde et al.
2008/0097273 A1 4/2008 Levin et al.
2008/0097562 A1 4/2008 Tan
2008/0119421 A1 5/2008 Tuszynski et al.
2008/0132748 A1 6/2008 Shifflette
2008/0132749 A1 6/2008 Hegde et al.
2008/0167679 A1 7/2008 Papp
2008/0167711 A1 7/2008 Roorda
2008/0188923 A1 8/2008 Chu
2008/0200750 A1 8/2008 James
2008/0208329 A1 8/2008 Bishop et al.
2008/0228026 A1 9/2008 Manera et al.
2008/0240947 A1 10/2008 Allaire et al.

(56) References Cited

U.S. PATENT DOCUMENTS

2008/0243030 A1 10/2008 Seibel et al.
2008/0275295 A1 11/2008 Gertner
2008/0275354 A1 11/2008 Thuramalla et al.
2008/0296433 A1 12/2008 Brenner et al.
2008/0300677 A1 12/2008 Schrayer
2009/0012460 A1 1/2009 Steck et al.
2009/0061072 A1 3/2009 Isch et al.
2009/0063402 A1 3/2009 Hayter
2009/0082723 A1 3/2009 Krogh et al.
2009/0143635 A1 6/2009 Benkowski et al.
2009/0171448 A1 7/2009 El
2009/0177028 A1 7/2009 White
2009/0182307 A1 7/2009 Yap et al.
2009/0188964 A1 7/2009 Orlov
2009/0259089 A1 10/2009 Gelbart et al.
2010/0016703 A1 1/2010 Batkin et al.
2010/0022943 A1 1/2010 Mauch et al.
2010/0042037 A1 2/2010 Felt et al.
2010/0076380 A1 3/2010 Hui
2010/0084326 A1 4/2010 Takesawa
2010/0087742 A1 4/2010 Bishop et al.
2010/0105978 A1 4/2010 Matsui et al.
2010/0152523 A1 6/2010 MacDonald et al.
2010/0152525 A1 6/2010 Weizman et al.
2010/0152526 A1 6/2010 Pacella et al.
2010/0160751 A1 6/2010 Hete et al.
2010/0184318 A1 7/2010 Bogart et al.
2010/0185220 A1 7/2010 Naghavi et al.
2010/0222635 A1 9/2010 Poirier
2010/0222878 A1 9/2010 Poirier
2010/0249489 A1 9/2010 Jarvik
2011/0098548 A1 4/2011 Budiman et al.
2011/0106115 A1 5/2011 Haselby et al.
2011/0106120 A1 5/2011 Haselby et al.
2011/0178596 A1 7/2011 Hauck et al.
2011/0224655 A1 9/2011 Asirvatham et al.
2011/0297599 A1 12/2011 Lo et al.
2011/0301625 A1 12/2011 Mauch et al.
2011/0304240 A1 12/2011 Meitav et al.
2012/0022316 A1 1/2012 Aboul-Hosn et al.
2012/0028908 A1 2/2012 Viswanath et al.
2012/0039711 A1 2/2012 Roehn
2012/0109060 A1 5/2012 Kick et al.
2012/0165641 A1 6/2012 Burnett et al.
2012/0179184 A1 7/2012 Orlov
2012/0184803 A1 7/2012 Simon et al.
2012/0190918 A1 7/2012 Oepen et al.
2012/0239139 A1 9/2012 Whendt et al.
2012/0252709 A1 10/2012 Felts et al.
2012/0289928 A1 11/2012 Wright et al.
2012/0302458 A1 11/2012 Adamczyk et al.
2012/0330683 A1 12/2012 Ledwidge et al.
2013/0023373 A1 1/2013 Janek
2013/0040407 A1 2/2013 Brophy et al.
2013/0053693 A1 2/2013 Breznock et al.
2013/0144144 A1 6/2013 Laster et al.
2013/0211489 A1 8/2013 Makower et al.
2013/0233798 A1 9/2013 Wiktor et al.
2013/0245360 A1 9/2013 Schumacher
2013/0267892 A1 10/2013 Woolford
2013/0281761 A1 10/2013 Kapur
2013/0289696 A1 10/2013 Maggard et al.
2013/0310845 A1 11/2013 Thor et al.
2013/0317604 A1 11/2013 Min et al.
2013/0344047 A1 12/2013 Pacetti et al.
2014/0017200 A1 1/2014 Michal et al.
2014/0039465 A1 2/2014 Schulz et al.
2014/0039603 A1 2/2014 Wang
2014/0051908 A1 2/2014 Khanal et al.
2014/0058190 A1 2/2014 Gohean et al.
2014/0066693 A1 3/2014 Goldfarb et al.
2014/0128659 A1 5/2014 Heuring et al.
2014/0128795 A1 5/2014 Keren et al.
2014/0142617 A1 5/2014 Larsen et al.
2014/0148638 A1 5/2014 LaRose et al.
2014/0163664 A1 6/2014 Goldsmith
2014/0190523 A1 7/2014 Garvey et al.
2014/0194678 A1 7/2014 Wildhirt et al.
2014/0194717 A1 7/2014 Wildhirt et al.
2014/0199377 A1 7/2014 Stankus et al.
2014/0200655 A1 7/2014 Webler et al.
2014/0207232 A1 7/2014 Garrigue
2014/0228741 A1 8/2014 Frankowski et al.
2014/0243970 A1 8/2014 Yanal
2014/0255176 A1 9/2014 Bredenbreuker et al.
2014/0260551 A1 9/2014 Gray et al.
2014/0275721 A1 9/2014 Yanal et al.
2014/0275725 A1 9/2014 Schenck et al.
2014/0288354 A1 9/2014 Timms et al.
2014/0309481 A1 10/2014 Medvedev et al.
2014/0336444 A1 11/2014 Bonde
2014/0336486 A1 11/2014 Ouyang et al.
2014/0336747 A1 11/2014 Rapoza et al.
2014/0341726 A1 11/2014 Wu et al.
2014/0350328 A1 11/2014 Mohl
2014/0357938 A1 12/2014 Pilla et al.
2014/0370073 A1 12/2014 Tang et al.
2015/0005571 A1 1/2015 Jeffery et al.
2015/0018747 A1 1/2015 Michal et al.
2015/0031938 A1 1/2015 Crosby et al.
2015/0051437 A1 2/2015 Miyakoshi et al.
2015/0068069 A1 3/2015 Tran et al.
2015/0080639 A1 3/2015 Radziemski et al.
2015/0080743 A1 3/2015 Siess
2015/0087890 A1 3/2015 Spanier et al.
2015/0101645 A1 4/2015 Neville et al.
2015/0112210 A1 4/2015 Webler
2015/0119859 A1 4/2015 Cajamarca et al.
2015/0120323 A1 4/2015 Galasso et al.
2015/0134048 A1 5/2015 Ding
2015/0152878 A1 6/2015 McBride et al.
2015/0159643 A1 6/2015 Koob
2015/0174060 A1 6/2015 Heit et al.
2015/0191607 A1 7/2015 McDaniel
2015/0207331 A1 7/2015 Petersen
2015/0216685 A1 8/2015 Spence et al.
2015/0222128 A1 8/2015 Hansen
2015/0222139 A1 8/2015 Petersen et al.
2015/0226691 A1 8/2015 Wang et al.
2015/0230709 A1 8/2015 Milner et al.
2015/0231317 A1 8/2015 Schima et al.
2015/0238671 A1 8/2015 Mesallum
2015/0265757 A1 9/2015 Dowling et al.
2015/0283027 A1 10/2015 Lampe et al.
2015/0283309 A1* 10/2015 Look ...................... A61B 17/22 606/127
2015/0285258 A1 10/2015 Foster
2015/0290370 A1 10/2015 Crunkleton et al.
2015/0290377 A1 10/2015 Kearsley et al.
2015/0306291 A1 10/2015 Bonde et al.
2015/0320926 A1 11/2015 Fitzpatrick et al.
2015/0328382 A1 11/2015 Corbett et al.
2015/0335803 A1 11/2015 Yamane
2015/0364861 A1 12/2015 Lucke et al.
2015/0366495 A1 12/2015 Gable, III et al.
2015/0367050 A1 12/2015 Bulent et al.
2015/0368335 A1 12/2015 Banerjee et al.
2015/0374892 A1 12/2015 Yanai et al.
2016/0022887 A1 1/2016 Wampler
2016/0022890 A1 1/2016 Schwammenthal et al.
2016/0030649 A1 2/2016 Zeng
2016/0038315 A1 2/2016 Consigny et al.
2016/0045098 A1 2/2016 Tsubouchi
2016/0045652 A1 2/2016 Comen
2016/0045654 A1 2/2016 Connor
2016/0053763 A1 2/2016 Toellner
2016/0058434 A1 3/2016 Delaloye et al.
2016/0067395 A1 3/2016 Jimenez et al.
2016/0085714 A1 3/2016 Goodnow et al.
2016/0175044 A1 6/2016 Abunassar et al.
2016/0182158 A1 6/2016 Lee et al.
2016/0184499 A1 6/2016 Ricci et al.
2016/0199543 A1 7/2016 Venkateswara-Rao
2016/0199556 A1 7/2016 Ayre et al.

(56) References Cited

U.S. PATENT DOCUMENTS

2016/0199557 A1 7/2016 Bluvshtein et al.
2016/0203275 A1 7/2016 Benjamin et al.
2016/0206798 A1 7/2016 Williams et al.
2016/0220269 A1 8/2016 Labropoulos et al.
2016/0220785 A1 8/2016 Fabro
2016/0222969 A1 8/2016 Heide et al.
2016/0250399 A1 9/2016 Tiller et al.
2016/0250400 A1 9/2016 Schumacher
2016/0251720 A1 9/2016 Schulze et al.
2016/0256620 A1 9/2016 Scheckel et al.
2016/0263299 A1 9/2016 Xu et al.
2016/0271161 A1 9/2016 Dobson
2016/0271309 A1 9/2016 Throckmorton et al.
2016/0279310 A1 9/2016 Scheckel et al.
2016/0303301 A1 10/2016 Bluvshtein et al.
2016/0308403 A1 10/2016 Bluvshtein et al.
2016/0317291 A1 11/2016 Bishop et al.
2016/0317333 A1 11/2016 Ainsworth et al.
2016/0325034 A1 11/2016 Wiktor et al.
2016/0348688 A1 12/2016 Schumacher et al.
2016/0354526 A1 12/2016 Whisenant et al.
2016/0375187 A1 12/2016 Lee et al.
2017/0000361 A1 1/2017 Meyering et al.
2017/0000935 A1 1/2017 Vasilyev et al.
2017/0007552 A1 1/2017 Slepian
2017/0007762 A1 1/2017 Hayter et al.
2017/0014401 A1 1/2017 Dalton et al.
2017/0014562 A1 1/2017 Liebing
2017/0021074 A1 1/2017 Opfermann et al.
2017/0028114 A1 2/2017 Göllner et al.
2017/0028115 A1 2/2017 Muller
2017/0035952 A1 2/2017 Muller
2017/0035954 A1 2/2017 Muller et al.
2017/0037860 A1 2/2017 Toellner
2017/0043076 A1 2/2017 Wampler et al.
2017/0063143 A1 3/2017 Hoarau et al.
2017/0080136 A1 3/2017 Janeczek et al.
2017/0100527 A1 4/2017 Schwammenthal et al.
2017/0112984 A1 4/2017 Vargas Fonseca
2017/0119945 A1 5/2017 Neumann
2017/0119946 A1 5/2017 McChrystal et al.
2017/0136165 A1 5/2017 Hansen et al.
2017/0136225 A1 5/2017 Siess et al.
2017/0143883 A1 5/2017 Spence
2017/0143952 A1 5/2017 Siess et al.
2017/0157309 A1 6/2017 Begg et al.
2017/0173242 A1 6/2017 Anderson et al.
2017/0181760 A1* 6/2017 Look .............. A61B 17/320758
2017/0193184 A1 7/2017 Hayter et al.
2017/0196638 A1 7/2017 Serna et al.
2017/0202575 A1 7/2017 Stanfield et al.
2017/0215918 A1 8/2017 Tao et al.
2017/0224896 A1 8/2017 Graham et al.
2017/0232168 A1 8/2017 Reichenbach et al.
2017/0232169 A1 8/2017 Muller
2017/0232172 A1 8/2017 Mesallum
2017/0239407 A1 8/2017 Hayward
2017/0250575 A1 8/2017 Wong et al.
2017/0265994 A1 9/2017 Krone
2017/0274128 A1 9/2017 Tamburino et al.
2017/0281025 A9 10/2017 Glover et al.
2017/0281841 A1 10/2017 Larose et al.
2017/0281842 A1 10/2017 Larose et al.
2017/0290964 A1 10/2017 Barry
2017/0296227 A1 10/2017 Osypka
2017/0296725 A1 10/2017 Peters et al.
2017/0312106 A1 11/2017 Gomez et al.
2017/0312416 A1 11/2017 Strueber
2017/0312492 A1 11/2017 Fantuzzi et al.
2017/0319113 A1 11/2017 Hurd et al.
2017/0323713 A1 11/2017 Moeller et al.
2017/0325943 A1 11/2017 Robin et al.
2017/0333607 A1 11/2017 Zarins
2017/0333673 A1 11/2017 Tuval et al.
2017/0340788 A1 11/2017 Korakianitis et al.
2017/0340789 A1 11/2017 Bonde et al.
2017/0340790 A1 11/2017 Wiesener et al.
2017/0348470 A1 12/2017 D'Ambrosio et al.
2017/0360309 A1 12/2017 Moore et al.
2017/0361001 A1 12/2017 Canatella et al.
2017/0361011 A1 12/2017 Muennich et al.
2017/0363103 A1 12/2017 Canatella et al.
2017/0363210 A1 12/2017 Durst et al.
2017/0363620 A1 12/2017 Beshiri et al.
2017/0368246 A1 12/2017 Criscione et al.
2017/0370365 A1 12/2017 Fritz et al.
2018/0001003 A1 1/2018 Moran et al.
2018/0001007 A1 1/2018 Stratton
2018/0001012 A1 1/2018 Ardehali
2018/0001062 A1 1/2018 O'Carrol et al.
2018/0015214 A1 1/2018 Lynch
2018/0021494 A1 1/2018 Muller et al.
2018/0021495 A1 1/2018 Muller et al.
2018/0021497 A1 1/2018 Nunez et al.
2018/0028736 A1 2/2018 Wong et al.
2018/0035926 A1 2/2018 Stafford
2018/0040418 A1 2/2018 Hansen et al.
2018/0047282 A1 2/2018 He et al.
2018/0050139 A1 2/2018 Siess et al.
2018/0050140 A1 2/2018 Siess et al.
2018/0050142 A1 2/2018 Siess et al.
2018/0055383 A1 3/2018 Manera
2018/0055983 A1 3/2018 Bourque
2018/0058437 A1 3/2018 Ellers et al.
2018/0064862 A1 3/2018 Keenan et al.
2018/0071020 A1 3/2018 Laufer et al.
2018/0078159 A1 3/2018 Edelman et al.
2018/0080326 A1 3/2018 Schumacher et al.
2018/0085505 A1 3/2018 Casas
2018/0085507 A1 3/2018 Casas et al.
2018/0085509 A1 3/2018 Petersen
2018/0093026 A1 4/2018 Angwin et al.
2018/0097368 A1 4/2018 Hansen
2018/0099076 A1 4/2018 Larose
2018/0099078 A1 4/2018 Tuseth et al.
2018/0100507 A1 4/2018 Wu et al.
2018/0103611 A1 4/2018 Mainini et al.
2018/0103870 A1 4/2018 Limaye et al.
2018/0108275 A1 4/2018 Newberry et al.
2018/0110514 A1 4/2018 Hoarau et al.
2018/0114426 A1 4/2018 Lee
2018/0133380 A1 5/2018 Liebing
2018/0140759 A1 5/2018 Kaiser et al.
2018/0140801 A1 5/2018 Voss et al.
2018/0146968 A1 5/2018 Nitzan et al.
2018/0149164 A1 5/2018 Siess
2018/0149165 A1 5/2018 Siess et al.
2018/0154051 A1 6/2018 Hossainy et al.
2018/0154128 A1 6/2018 Woo et al.
2018/0161540 A1 6/2018 Fantuzzi et al.
2018/0161555 A1 6/2018 Zhadkevich
2018/0168469 A1 6/2018 Granegger
2018/0169312 A1 6/2018 Barry
2018/0169313 A1 6/2018 Schwammenthal et al.
2018/0193543 A1 7/2018 Sun
2018/0193614 A1 7/2018 Nitzan et al.
2018/0193616 A1 7/2018 Nitzan et al.
2018/0200420 A1 7/2018 Di Paola et al.
2018/0200422 A1 7/2018 Nguyen et al.
2018/0202962 A1 7/2018 Simmons et al.
2018/0207334 A1 7/2018 Siess
2018/0207337 A1 7/2018 Spence et al.
2018/0207338 A1 7/2018 Bluvshtein et al.
2018/0226997 A1 8/2018 Jia
2018/0228953 A1 8/2018 Siess et al.
2018/0228957 A1 8/2018 Colella
2018/0242891 A1 8/2018 Bernstein et al.
2018/0242976 A1 8/2018 Kizuka
2018/0243086 A1 8/2018 Barbarino et al.
2018/0243488 A1 8/2018 Callaway et al.
2018/0243489 A1 8/2018 Haddadi
2018/0243490 A1 8/2018 Kallenbach et al.
2018/0243492 A1 8/2018 Salys
2018/0250457 A1 9/2018 Morello et al.

(56) References Cited

U.S. PATENT DOCUMENTS

2018/0250458 A1 9/2018 Petersen et al.
2018/0256242 A1 9/2018 Bluvshtein et al.
2018/0256794 A1 9/2018 Rodefeld
2018/0256795 A1 9/2018 Schade et al.
2018/0256797 A1* 9/2018 Schenck ................ A61M 1/72
2018/0256798 A1 9/2018 Botterbusch et al.
2018/0256859 A1 9/2018 Korkuch
2018/0264183 A1 9/2018 Jahangir
2018/0264184 A1 9/2018 Jeffries et al.
2018/0269692 A1 9/2018 Petersen et al.
2018/0280598 A1 10/2018 Curran et al.
2018/0280599 A1 10/2018 Harjes et al.
2018/0280600 A1 10/2018 Harjes et al.
2018/0280601 A1 10/2018 Harjes et al.
2018/0280604 A1 10/2018 Hobro et al.
2018/0289295 A1 10/2018 Hoss et al.
2018/0289876 A1 10/2018 Nguyen et al.
2018/0289877 A1 10/2018 Schumacher et al.
2018/0296572 A1 10/2018 Deisher
2018/0303990 A1 10/2018 Siess et al.
2019/0030231 A1 1/2019 Aboul-Hosn et al.
2019/0070345 A1 3/2019 McBride et al.
2019/0076167 A1 3/2019 Fantuzzi et al.
2019/0083690 A1 3/2019 Siess et al.
2019/0167873 A1 6/2019 Koike et al.
2019/0209751 A1 7/2019 Tuval et al.
2019/0290822 A1 9/2019 Igarashi
2019/0321531 A1 10/2019 Cambronne et al.
2020/0029951 A1 1/2020 Bessler et al.
2020/0030510 A1 1/2020 Higgins
2020/0038568 A1 2/2020 Higgins et al.
2020/0121835 A1 4/2020 Farago et al.
2020/0237981 A1 7/2020 Tuval et al.
2020/0246527 A1 8/2020 Hildebrand et al.
2020/0316268 A1 10/2020 Antoni et al.
2020/0391014 A1 12/2020 Walters et al.
2021/0008261 A1 1/2021 Calomeni et al.
2021/0023285 A1 1/2021 Brandt
2021/0038786 A1 2/2021 Calomeni et al.
2021/0052794 A1 2/2021 Tuval et al.
2021/0113212 A1 4/2021 Lashinski et al.
2021/0121679 A1 4/2021 Mohl et al.
2021/0138201 A1 5/2021 Schumacher et al.
2021/0236797 A1 8/2021 D'Ambrosio et al.
2021/0244937 A1 8/2021 Calomeni et al.
2021/0252271 A1 8/2021 Wallin et al.
2021/0252274 A1 8/2021 Dhaliwal et al.
2021/0308444 A1 10/2021 Saul et al.
2022/0080178 A1 3/2022 Salahieh et al.
2022/0105337 A1 4/2022 Salahieh et al.
2022/0203084 A1 6/2022 Zarins et al.
2022/0233841 A1 7/2022 Hildebrand et al.
2022/0273933 A1 9/2022 Ryan et al.
2022/0313980 A1 10/2022 Hildebrand et al.
2023/0001177 A1 1/2023 Robinson et al.
2023/0033471 A1 2/2023 Ryan et al.
2023/0218886 A1 7/2023 Robinson et al.
2023/0264012 A1 8/2023 Brandt
2023/0390544 A1 12/2023 Hildebrand et al.
2023/0405298 A1 12/2023 Hildebrand et al.
2023/0414920 A1 12/2023 Salahleh et al.
2024/0001101 A1 1/2024 Wallin et al.
2024/0115849 A1 4/2024 Dhaliwal et al.
2024/0139499 A1 5/2024 Salahleh et al.
2024/0149046 A1 5/2024 Calomeni et al.
2024/0157117 A1 5/2024 Ryan et al.
2024/0173540 A1 5/2024 Wallin et al.
2024/0181238 A1 6/2024 Ryan et al.

FOREIGN PATENT DOCUMENTS

CA 3014105 A1 8/2017
CN 1040073 A 2/1990
CN 1008307 B 6/1990
CN 1053108 A 7/1991
CN 1105103 A 7/1995
CN 1146329 A 4/1997
CN 1179708 A 4/1998
CN 2326258 Y 6/1999
CN 1222862 A 7/1999
CN 1045058 C 9/1999
CN 1235849 A 11/1999
CN 2361290 Y 2/2000
CN 1254598 A 5/2000
CN 2386827 Y 7/2000
CN 2412579 Y 1/2001
CN 2417173 Y 1/2001
CN 1310647 A 8/2001
CN 1342497 A 4/2002
CN 1088795 C 8/2002
CN 2504815 Y 8/2002
CN 1376523 A 10/2002
CN 1097138 C 12/2002
CN 1105581 C 4/2003
CN 1421248 A 6/2003
CN 2558386 Y 7/2003
CN 1118304 C 8/2003
CN 1436048 A 8/2003
CN 1120729 C 9/2003
CN 2574609 Y 9/2003
CN 1140228 C 3/2004
CN 1161581 C 8/2004
CN 1167472 C 9/2004
CN 1527906 A 9/2004
CN 1559361 A 1/2005
CN 1559626 A 1/2005
CN 1572331 A 2/2005
CN 1202871 C 5/2005
CN 1679974 A 10/2005
CN 1694338 A 11/2005
CN 1705462 A 12/2005
CN 1239133 C 2/2006
CN 1239209 C 2/2006
CN 2754637 Y 2/2006
CN 1244381 C 3/2006
CN 1249339 C 4/2006
CN 2776418 Y 5/2006
CN 2787222 Y 6/2006
CN 1799652 A 7/2006
CN 1806774 A 7/2006
CN 1826463 A 8/2006
CN 1833735 A 9/2006
CN 1833736 A 9/2006
CN 2831716 Y 10/2006
CN 1874805 A 12/2006
CN 1301583 C 2/2007
CN 1921947 A 2/2007
CN 2880096 Y 3/2007
CN 2899800 Y 5/2007
CN 101001765 A 7/2007
CN 1329666 C 8/2007
CN 101024098 A 8/2007
CN 101031302 A 9/2007
CN 101112628 A 1/2008
CN 101121045 A 2/2008
CN 101124002 A 2/2008
CN 101132830 A 2/2008
CN 100382855 C 4/2008
CN 101256992 A 9/2008
CN 100429406 C 10/2008
CN 100439717 C 12/2008
CN 100472042 C 3/2009
CN 201208423 Y 3/2009
CN 100488577 C 5/2009
CN 201230980 Y 5/2009
CN 201239369 Y 5/2009
CN 201246310 Y 5/2009
CN 101448535 A 6/2009
CN 101522115 A 9/2009
CN 101534883 A 9/2009
CN 201308666 Y 9/2009
CN 101563605 A 10/2009
CN 100558416 C 11/2009
CN 100566765 C 12/2009

(56) References Cited

FOREIGN PATENT DOCUMENTS

| | | | |
|---|---|---|---|
| CN | 101595276 | A | 12/2009 |
| CN | 101631578 | A | 1/2010 |
| CN | 101652069 | A | 2/2010 |
| CN | 101678025 | A | 3/2010 |
| CN | 101687791 | A | 3/2010 |
| CN | 101244296 | B | 6/2010 |
| CN | 101730552 | A | 6/2010 |
| CN | 101208058 | B | 8/2010 |
| CN | 101808515 | A | 8/2010 |
| CN | 101401981 | B | 9/2010 |
| CN | 101843528 | A | 9/2010 |
| CN | 101232952 | B | 11/2010 |
| CN | 101361994 | B | 11/2010 |
| CN | 201618200 | U | 11/2010 |
| CN | 201710717 | U | 1/2011 |
| CN | 101417155 | B | 2/2011 |
| CN | 101581307 | B | 4/2011 |
| CN | 102065923 | A | 5/2011 |
| CN | 101269245 | B | 7/2011 |
| CN | 101618240 | B | 8/2011 |
| CN | 102166379 | A | 8/2011 |
| CN | 101484093 | B | 9/2011 |
| CN | 102292053 | A | 12/2011 |
| CN | 102422018 | A | 4/2012 |
| CN | 102438673 | A | 5/2012 |
| CN | 102475923 | A | 5/2012 |
| CN | 202218993 | U | 5/2012 |
| CN | 101983732 | B | 7/2012 |
| CN | 102553005 | A | 7/2012 |
| CN | 101590295 | B | 8/2012 |
| CN | 101822854 | B | 9/2012 |
| CN | 101822855 | B | 9/2012 |
| CN | 101189431 | B | 10/2012 |
| CN | 101810891 | B | 10/2012 |
| CN | 102711862 | A | 10/2012 |
| CN | 102711894 | A | 10/2012 |
| CN | 102869318 | A | 1/2013 |
| CN | 102917748 | A | 2/2013 |
| CN | 102088920 | B | 4/2013 |
| CN | 103026234 | A | 4/2013 |
| CN | 103068417 | A | 4/2013 |
| CN | 103172739 | A | 6/2013 |
| CN | 101420993 | B | 7/2013 |
| CN | 103206402 | A | 7/2013 |
| CN | 103228300 | A | 7/2013 |
| CN | 103356306 | A | 10/2013 |
| CN | 103381277 | A | 11/2013 |
| CN | 103432637 | A | 12/2013 |
| CN | 103437951 | A | 12/2013 |
| CN | 103446635 | A | 12/2013 |
| CN | 103458832 | A | 12/2013 |
| CN | 102319457 | B | 1/2014 |
| CN | 103509116 | A | 1/2014 |
| CN | 103541857 | A | 1/2014 |
| CN | 103635212 | A | 3/2014 |
| CN | 203507200 | U | 4/2014 |
| CN | 203539803 | U | 4/2014 |
| CN | 203591299 | U | 5/2014 |
| CN | 102317629 | B | 8/2014 |
| CN | 203756589 | U | 8/2014 |
| CN | 104043153 | A | 9/2014 |
| CN | 203829160 | U | 9/2014 |
| CN | 104105511 | A | 10/2014 |
| CN | 203935281 | U | 11/2014 |
| CN | 104185456 | A | 12/2014 |
| CN | 104208763 | A | 12/2014 |
| CN | 203971002 | U | 12/2014 |
| CN | 204050452 | U | 12/2014 |
| CN | 102271728 | B | 1/2015 |
| CN | 102294057 | B | 1/2015 |
| CN | 104271075 | A | 1/2015 |
| CN | 102588255 | B | 3/2015 |
| CN | 104470454 | A | 3/2015 |
| CN | 102300501 | B | 4/2015 |
| CN | 103055363 | B | 4/2015 |
| CN | 104473676 | A | 4/2015 |
| CN | 104524663 | A | 4/2015 |
| CN | 204293210 | U | 4/2015 |
| CN | 102686316 | B | 5/2015 |
| CN | 104586469 | A | 5/2015 |
| CN | 104602987 | A | 5/2015 |
| CN | 102458275 | B | 6/2015 |
| CN | 102458498 | B | 6/2015 |
| CN | 104684607 | A | 6/2015 |
| CN | 104721899 | A | 6/2015 |
| CN | 204419151 | U | 6/2015 |
| CN | 102397598 | B | 7/2015 |
| CN | 103446634 | B | 7/2015 |
| CN | 104758029 | A | 7/2015 |
| CN | 104771797 | A | 7/2015 |
| CN | 101868628 | B | 8/2015 |
| CN | 103706018 | B | 9/2015 |
| CN | 104955420 | A | 9/2015 |
| CN | 104984425 | A | 10/2015 |
| CN | 104997550 | A | 10/2015 |
| CN | 105007960 | A | 10/2015 |
| CN | 105142719 | A | 12/2015 |
| CN | 105208927 | A | 12/2015 |
| CN | 102176933 | B | 1/2016 |
| CN | 102947092 | B | 1/2016 |
| CN | 103717837 | B | 1/2016 |
| CN | 105228688 | A | 1/2016 |
| CN | 105283149 | A | 1/2016 |
| CN | 204972635 | U | 1/2016 |
| CN | 103228232 | B | 2/2016 |
| CN | 103355925 | B | 2/2016 |
| CN | 105311692 | A | 2/2016 |
| CN | 102257279 | B | 3/2016 |
| CN | 102472719 | B | 3/2016 |
| CN | 103154738 | B | 3/2016 |
| CN | 105451787 | A | 3/2016 |
| CN | 205083494 | U | 3/2016 |
| CN | 103850979 | B | 4/2016 |
| CN | 105477706 | A | 4/2016 |
| CN | 105517589 | A | 4/2016 |
| CN | 205163763 | U | 4/2016 |
| CN | 103002833 | B | 5/2016 |
| CN | 103861163 | B | 5/2016 |
| CN | 105555204 | A | 5/2016 |
| CN | 205215814 | U | 5/2016 |
| CN | 102940911 | B | 6/2016 |
| CN | 105641762 | A | 6/2016 |
| CN | 105641763 | A | 6/2016 |
| CN | 105662439 | A | 6/2016 |
| CN | 105709287 | A | 6/2016 |
| CN | 105722477 | A | 6/2016 |
| CN | 205322884 | U | 6/2016 |
| CN | 104069555 | B | 7/2016 |
| CN | 105744915 | A | 7/2016 |
| CN | 105790453 | A | 7/2016 |
| CN | 105792780 | A | 7/2016 |
| CN | 105792864 | A | 7/2016 |
| CN | 103260666 | B | 8/2016 |
| CN | 103732171 | B | 8/2016 |
| CN | 103928971 | B | 8/2016 |
| CN | 105833370 | A | 8/2016 |
| CN | 205411785 | U | 8/2016 |
| CN | 205460099 | U | 8/2016 |
| CN | 205528886 | U | 8/2016 |
| CN | 103889369 | B | 9/2016 |
| CN | 104849482 | B | 9/2016 |
| CN | 105980660 | A | 9/2016 |
| CN | 106075621 | A | 11/2016 |
| CN | 106102657 | A | 11/2016 |
| CN | 205681272 | U | 11/2016 |
| CN | 205698666 | U | 11/2016 |
| CN | 205698725 | U | 11/2016 |
| CN | 205753678 | U | 11/2016 |
| CN | 106214288 | A | 12/2016 |
| CN | 106256321 | A | 12/2016 |
| CN | 205779766 | U | 12/2016 |
| CN | 106334224 | A | 1/2017 |
| CN | 205867186 | U | 1/2017 |
| CN | 205876589 | U | 1/2017 |

(56) References Cited

FOREIGN PATENT DOCUMENTS

CN 103281971 B 2/2017
CN 106390218 A 2/2017
CN 103533970 B 3/2017
CN 104826183 B 3/2017
CN 106512117 A 3/2017
CN 106581840 A 4/2017
CN 104068947 B 5/2017
CN 106620912 A 5/2017
CN 106691363 A 5/2017
CN 106716137 A 5/2017
CN 106794293 A 5/2017
CN 104225696 B 6/2017
CN 104918578 B 6/2017
CN 105915005 B 6/2017
CN 106902404 A 6/2017
CN 106955140 A 7/2017
CN 206325049 U 7/2017
CN 206355093 U 7/2017
CN 105377321 B 8/2017
CN 107050543 A 8/2017
CN 107050544 A 8/2017
CN 107080870 A 8/2017
CN 107080871 A 8/2017
CN 107110875 A 8/2017
CN 206414547 U 8/2017
CN 206443963 U 8/2017
CN 103930214 B 9/2017
CN 104619361 B 9/2017
CN 104936550 B 9/2017
CN 105188618 B 9/2017
CN 107115162 A 9/2017
CN 107126299 A 9/2017
CN 107126588 A 9/2017
CN 107134208 A 9/2017
CN 107157623 A 9/2017
CN 103857363 B 10/2017
CN 104768500 B 10/2017
CN 105008841 B 10/2017
CN 105492036 B 10/2017
CN 107252339 A 10/2017
CN 107281567 A 10/2017
CN 206592332 U 10/2017
CN 107349484 A 11/2017
CN 206660203 U 11/2017
CN 105287050 B 12/2017
CN 105597172 B 12/2017
CN 105854097 B 12/2017
CN 107412892 A 12/2017
CN 107440681 A 12/2017
CN 107496054 A 12/2017
CN 104602647 B 1/2018
CN 106061523 B 1/2018
CN 107551341 A 1/2018
CN 206934393 U 1/2018
CN 107693868 A 2/2018
CN 107693869 A 2/2018
CN 107708765 A 2/2018
CN 207018256 U 2/2018
CN 106029120 B 3/2018
CN 107753153 A 3/2018
CN 107754071 A 3/2018
CN 107798980 A 3/2018
CN 107835826 A 3/2018
CN 107837430 A 3/2018
CN 107862963 A 3/2018
CN 207125933 U 3/2018
CN 207136890 U 3/2018
CN 105120796 B 4/2018
CN 105214153 B 4/2018
CN 107865988 A 4/2018
CN 107886825 A 4/2018
CN 107913442 A 4/2018
CN 107921195 A 4/2018
CN 107923311 A 4/2018
CN 108025120 A 5/2018
CN 108025123 A 5/2018
CN 108066834 A 5/2018
CN 207410652 U 5/2018
CN 104470579 B 6/2018
CN 105188604 B 6/2018
CN 105492909 B 6/2018
CN 105498002 B 6/2018
CN 106535824 B 6/2018
CN 108136110 A 6/2018
CN 108144146 A 6/2018
CN 108175884 A 6/2018
CN 106028807 B 7/2018
CN 106310410 B 7/2018
CN 108273148 A 7/2018
CN 108310486 A 7/2018
CN 108348667 A 7/2018
CN 207614108 U 7/2018
CN 105640635 B 8/2018
CN 105923112 B 8/2018
CN 108367106 A 8/2018
CN 108430533 A 8/2018
CN 108457844 A 8/2018
CN 108472138 A 8/2018
CN 108472395 A 8/2018
CN 108472424 A 8/2018
CN 207708246 U 8/2018
CN 207708250 U 8/2018
CN 105407937 B 9/2018
CN 105902298 B 9/2018
CN 106420113 B 9/2018
CN 106510902 B 9/2018
CN 108525039 A 9/2018
CN 108525040 A 9/2018
CN 108601653 A 9/2018
CN 108601872 A 9/2018
CN 108601874 A 9/2018
CN 108601875 A 9/2018
CN 207924984 U 9/2018
CN 106377810 B 10/2018
EP 96495 B1 9/1986
EP 79373 B1 12/1986
EP 54049 B1 1/1988
EP 292510 A4 8/1989
EP 167562 B1 4/1990
EP 230532 B1 9/1990
EP 241950 B1 12/1990
EP 129779 B1 4/1991
EP 20264981 8/1991
EP 445782 A1 9/1991
EP 464714 A1 1/1992
EP 293592 B1 11/1992
EP 29772381 8/1993
EP 396575 B1 3/1994
EP 397668 B1 3/1994
EP 593574 A1 4/1994
EP 378251 B1 6/1994
EP 605621 A1 7/1994
EP 467999 B1 8/1994
EP 350282 B1 11/1994
EP 47863581 12/1994
EP 397720 B1 3/1995
EP 421558 B1 4/1995
EP 364799 B1 5/1995
EP 660726 A1 7/1995
EP 672386 A1 9/1995
EP 349581 B1 1/1996
EP 464973 B1 1/1996
EP 505270 B1 1/1996
EP 480101 B1 5/1996
EP 583781 B1 5/1996
EP 583012 B1 7/1996
EP 756500 A1 2/1997
EP 0764448 A2 3/1997
EP 767318 A2 4/1997
EP 788808 A2 8/1997
EP 799060 A1 10/1997
EP 823567 A1 2/1998
EP 832357 A1 4/1998
EP 841917 A1 5/1998

(56) References Cited

FOREIGN PATENT DOCUMENTS

EP 560000 B1 9/1998
EP 879012 A1 11/1998
EP 925078 A1 6/1999
EP 807141 B1 7/1999
EP 681654 B1 9/1999
EP 958066 A1 11/1999
EP 964718 A1 12/1999
EP 725657 B1 2/2000
EP 986409 A1 3/2000
EP 1007140 A1 6/2000
EP 1009466 A1 6/2000
EP 1027898 A1 8/2000
EP 1032437 A1 9/2000
EP 1045708 A1 10/2000
EP 1059885 A2 12/2000
EP 1139862 A1 10/2001
EP 1147317 A1 10/2001
EP 1148900 A1 10/2001
EP 74671281 10/2001
EP 699447 B1 11/2001
EP 591896 B1 2/2002
EP 731664 B1 2/2002
EP 797734 B1 2/2002
EP 1217954 A1 7/2002
EP 1231981 A1 8/2002
EP 950057 B1 11/2002
EP 751769 B1 1/2003
EP 1278461 A1 1/2003
EP 860046 B1 2/2003
EP 597881 B2 3/2003
EP 732949 B1 3/2003
EP 814701 B1 4/2003
EP 898479 B1 5/2003
EP 905379 B1 5/2003
EP 655625 B1 7/2003
EP 764448 B1 7/2003
EP 768091 B1 7/2003
EP 825888 B1 12/2003
EP 1379197 A1 1/2004
EP 1382366 A1 1/2004
EP 868145 B1 2/2004
EP 895480 B1 5/2004
EP 1441777 A2 8/2004
EP 916359 B1 9/2004
EP 1481698 A2 12/2004
EP 1482999 A1 12/2004
EP 1291027 B1 3/2005
EP 877633 B1 7/2005
EP 611228 B2 8/2005
EP 1212516 B1 10/2005
EP 1597457 A2 11/2005
EP 1261385 B1 2/2006
EP 1648309 A1 4/2006
EP 1354606 B1 6/2006
EP 1663081 A1 6/2006
EP 1321166 B1 7/2006
EP 1191956 B1 9/2006
EP 1722767 A2 11/2006
EP 1070510 B1 1/2007
EP 1317295 B1 1/2007
EP 1327455 B1 1/2007
EP 1776095 A1 4/2007
EP 1141670 B1 7/2007
EP 1807148 A2 7/2007
EP 1827448 A1 9/2007
EP 1374928 B1 12/2007
EP 1877133 A2 1/2008
EP 1379294 B1 5/2008
EP 1930034 A1 6/2008
EP 1318848 B1 7/2008
EP 1356859 B1 8/2008
EP 1955725 A2 8/2008
EP 2058017 A2 5/2009
EP 1731957 B1 8/2009
EP 1173238 B1 10/2009
EP 2043553 B1 3/2010
EP 2158491 A2 3/2010
EP 2178580 A2 4/2010
EP 2182844 A1 5/2010
EP 2194278 A1 6/2010
EP 2207578 A1 7/2010
EP 147195281 7/2010
EP 2216059 A1 8/2010
EP 2218469 A1 8/2010
EP 2219699 A1 8/2010
EP 2222635 A2 9/2010
EP 2222788 A1 9/2010
EP 2229965 A1 9/2010
EP 2235204 A1 10/2010
EP 1280581 B1 11/2010
EP 2246078 A1 11/2010
EP 2248544 A1 11/2010
EP 2252337 A1 11/2010
EP 2266640 A1 12/2010
EP 2269670 A1 1/2011
EP 2297583 A2 3/2011
EP 2298371 A1 3/2011
EP 2298372 A1 3/2011
EP 2298373 A1 3/2011
EP 2299119 A1 3/2011
EP 1464348 B1 4/2011
EP 2314330 A1 4/2011
EP 2314331 A1 4/2011
EP 2338539 A1 6/2011
EP 2338540 A1 6/2011
EP 2338541 A1 6/2011
EP 1654027 B1 7/2011
EP 2343091 A1 7/2011
EP 2347778 A1 7/2011
EP 1812094 B1 8/2011
EP 2349385 A1 8/2011
EP 2353626 A1 8/2011
EP 2356458 A1 8/2011
EP 2363157 A1 9/2011
EP 2366412 A2 9/2011
EP 1907049 B1 11/2011
EP 2388027 A1 11/2011
EP 2388029 A1 11/2011
EP 2399639 A1 12/2011
EP 1514571 B1 1/2012
EP 2407185 A1 1/2012
EP 2407186 A1 1/2012
EP 2407187 A1 1/2012
EP 2422735 A1 2/2012
EP 2322600 B1 3/2012
EP 2429603 A2 3/2012
EP 2459269 A1 6/2012
EP 2497521 A1 9/2012
EP 2140892 B1 10/2012
EP 2505228 A1 10/2012
EP 2150811 B1 1/2013
EP 1833529 B1 2/2013
EP 2554191 A1 2/2013
EP 2277463 B1 3/2013
EP 2564771 A1 3/2013
EP 2151257 B1 4/2013
EP 2575922 A2 4/2013
EP 1623730 B1 5/2013
EP 2606919 A1 6/2013
EP 2606920 A1 6/2013
EP 2607712 A1 6/2013
EP 1919550 B1 7/2013
EP 2620173 A1 7/2013
EP 1331017 B1 8/2013
EP 2101840 B1 9/2013
EP 2401003 B1 10/2013
EP 2654878 A2 10/2013
EP 2654883 A2 10/2013
EP 2671083 A1 12/2013
EP 1412001 B1 1/2014
EP 1942965 B1 1/2014
EP 2231222 B1 2/2014
EP 2697890 A2 2/2014
EP 1017433 B1 3/2014

(56) References Cited

FOREIGN PATENT DOCUMENTS

| | | | |
|---|---|---|---|
| EP | 1629855 | B1 | 4/2014 |
| EP | 2736581 | A2 | 6/2014 |
| EP | 2744460 | A1 | 6/2014 |
| EP | 2745869 | A1 | 6/2014 |
| EP | 1485613 | B1 | 7/2014 |
| EP | 1605988 | B1 | 8/2014 |
| EP | 2792696 | A2 | 10/2014 |
| EP | 2195043 | B1 | 12/2014 |
| EP | 1962949 | B1 | 2/2015 |
| EP | 2030641 | B1 | 2/2015 |
| EP | 2643927 | B1 | 4/2015 |
| EP | 2868331 | A2 | 5/2015 |
| EP | 1460972 | B1 | 6/2015 |
| EP | 2150569 | B1 | 6/2015 |
| EP | 2152783 | B1 | 6/2015 |
| EP | 2345439 | B1 | 6/2015 |
| EP | 2895215 | A2 | 7/2015 |
| EP | 1761306 | B1 | 8/2015 |
| EP | 2663347 | B1 | 8/2015 |
| EP | 2209508 | B1 | 9/2015 |
| EP | 2915129 | A1 | 9/2015 |
| EP | 2920421 | A2 | 9/2015 |
| EP | 2533732 | B1 | 11/2015 |
| EP | 1317305 | B1 | 12/2015 |
| EP | 1339443 | B1 | 1/2016 |
| EP | 2967284 | A1 | 1/2016 |
| EP | 2967547 | A1 | 1/2016 |
| EP | 2984731 | A1 | 2/2016 |
| EP | 2167158 | B1 | 3/2016 |
| EP | 2061531 | B1 | 4/2016 |
| EP | 2519274 | B1 | 4/2016 |
| EP | 1996252 | B1 | 5/2016 |
| EP | 2464395 | B1 | 5/2016 |
| EP | 3047873 | A1 | 7/2016 |
| EP | 3047911 | A1 | 7/2016 |
| EP | 2643053 | B1 | 8/2016 |
| EP | 2734251 | B1 | 8/2016 |
| EP | 3050537 | A1 | 8/2016 |
| EP | 1942128 | B1 | 9/2016 |
| EP | 2099509 | B1 | 9/2016 |
| EP | 2719403 | B1 | 9/2016 |
| EP | 3072210 | A1 | 9/2016 |
| EP | 3072211 | A1 | 9/2016 |
| EP | 2405140 | B1 | 10/2016 |
| EP | 2197507 | B1 | 11/2016 |
| EP | 2538086 | B1 | 11/2016 |
| EP | 3086834 | A1 | 11/2016 |
| EP | 2806911 | B1 | 12/2016 |
| EP | 3110468 | A1 | 1/2017 |
| EP | 3113808 | A1 | 1/2017 |
| EP | 3119452 | A1 | 1/2017 |
| EP | 3120811 | A2 | 1/2017 |
| EP | 3131595 | A1 | 2/2017 |
| EP | 3131596 | A1 | 2/2017 |
| EP | 3131599 | A1 | 2/2017 |
| EP | 3131600 | A1 | 2/2017 |
| EP | 3131615 | A1 | 2/2017 |
| EP | 2585129 | B1 | 3/2017 |
| EP | 2594799 | B1 | 3/2017 |
| EP | 3146987 | A1 | 3/2017 |
| EP | 3153190 | A1 | 4/2017 |
| EP | 3157597 | A1 | 4/2017 |
| EP | 3173110 | A1 | 5/2017 |
| EP | 2825107 | B1 | 7/2017 |
| EP | 3185924 | A1 | 7/2017 |
| EP | 3185925 | A1 | 7/2017 |
| EP | 3189526 | A1 | 7/2017 |
| EP | 3191164 | A1 | 7/2017 |
| EP | 2618001 | B1 | 8/2017 |
| EP | 3197602 | A1 | 8/2017 |
| EP | 3198677 | A1 | 8/2017 |
| EP | 3204989 | A1 | 8/2017 |
| EP | 3212250 | A1 | 9/2017 |
| EP | 3219339 | A1 | 9/2017 |
| EP | 3223880 | A1 | 10/2017 |
| EP | 3232948 | A1 | 10/2017 |
| EP | 1885409 | B1 | 11/2017 |
| EP | 2292282 | B1 | 11/2017 |
| EP | 2945661 | B1 | 11/2017 |
| EP | 3238764 | A1 | 11/2017 |
| EP | 3244814 | A1 | 11/2017 |
| EP | 3247420 | A1 | 11/2017 |
| EP | 3247421 | A2 | 11/2017 |
| EP | 3248628 | A1 | 11/2017 |
| EP | 2136861 | B1 | 12/2017 |
| EP | 3256183 | A1 | 12/2017 |
| EP | 3256184 | A1 | 12/2017 |
| EP | 3256185 | A1 | 12/2017 |
| EP | 3256186 | A1 | 12/2017 |
| EP | 3007742 | B1 | 1/2018 |
| EP | 3277200 | A1 | 2/2018 |
| EP | 3287155 | A1 | 2/2018 |
| EP | 2482916 | B1 | 3/2018 |
| EP | 2948202 | B1 | 3/2018 |
| EP | 3294367 | A1 | 3/2018 |
| EP | 2945662 | B1 | 4/2018 |
| EP | 3310409 | A1 | 4/2018 |
| EP | 3222301 | B1 | 5/2018 |
| EP | 3222302 | B1 | 5/2018 |
| EP | 3313471 | A1 | 5/2018 |
| EP | 3324840 | A1 | 5/2018 |
| EP | 3325035 | A1 | 5/2018 |
| EP | 3326487 | A1 | 5/2018 |
| EP | 1789129 | B1 | 6/2018 |
| EP | 1990358 | B1 | 6/2018 |
| EP | 3329953 | A1 | 6/2018 |
| EP | 3335647 | A2 | 6/2018 |
| EP | 3341069 | A1 | 7/2018 |
| EP | 3349839 | A1 | 7/2018 |
| EP | 2219698 | B1 | 8/2018 |
| EP | 2890420 | B1 | 8/2018 |
| EP | 3352808 | A1 | 8/2018 |
| EP | 3352835 | A1 | 8/2018 |
| EP | 3360233 | A1 | 8/2018 |
| EP | 3360515 | A1 | 8/2018 |
| EP | 1534381 | B1 | 9/2018 |
| EP | 3108909 | B1 | 9/2018 |
| EP | 3377001 | A1 | 9/2018 |
| EP | 3377002 | A1 | 9/2018 |
| EP | 3377134 | A1 | 9/2018 |
| EP | 3377135 | A1 | 9/2018 |
| EP | 3377136 | A1 | 9/2018 |
| EP | 2249746 | B1 | 10/2018 |
| EP | 2988795 | B1 | 10/2018 |
| EP | 3383300 | A1 | 10/2018 |
| EP | 3383448 | A1 | 10/2018 |
| EP | 3388005 | A1 | 10/2018 |
| EP | 3542835 | A1 | 9/2019 |
| FR | 2331995 | A2 | 6/1977 |
| JP | 64-52472 | A | 2/1989 |
| JP | 02289241 | A | 11/1990 |
| JP | 04176471 | A | 6/1992 |
| JP | 04224760 | A | 8/1992 |
| JP | H05-078996 | U | 10/1993 |
| JP | H11-062856 | A | 3/1999 |
| JP | 02888609 | B2 | 5/1999 |
| JP | 02927460 | B2 | 7/1999 |
| JP | H11-244376 | A | 9/1999 |
| JP | 2000102604 | A | 4/2000 |
| JP | 2000107281 | A | 4/2000 |
| JP | 2000283062 | A | 10/2000 |
| JP | 03131696 | B2 | 2/2001 |
| JP | 2001061957 | A | 3/2001 |
| JP | 2001090687 | A | 4/2001 |
| JP | 03174338 | B2 | 6/2001 |
| JP | 2001173402 | A | 6/2001 |
| JP | 2001523983 | A | 11/2001 |
| JP | 03278160 | B2 | 4/2002 |
| JP | 2002191123 | A | 7/2002 |
| JP | 03313061 | B2 | 8/2002 |
| JP | 2003047656 | A | 2/2003 |
| JP | 2003070906 | A | 3/2003 |
| JP | 2003205030 | A | 7/2003 |
| JP | 2004011525 | A | 1/2004 |

(56) References Cited

FOREIGN PATENT DOCUMENTS

JP 2004016426 A 1/2004
JP 2004028102 A 1/2004
JP 2004073400 A 3/2004
JP 2004209240 A 7/2004
JP 2004278375 A 10/2004
JP 03612581 B2 1/2005
JP 2005058617 A 3/2005
JP 2005192687 A 7/2005
JP 2005199076 A 7/2005
JP 2005348996 A 12/2005
JP 2006000631 A 1/2006
JP 03786289 B2 6/2006
JP 03803417 B2 8/2006
JP 2006280571 A 10/2006
JP 03854972 B2 12/2006
JP 2007044302 A 2/2007
JP 2007075541 A 3/2007
JP 2007089607 A 4/2007
JP 2007089973 A 4/2007
JP 2007222670 A 9/2007
JP 2007236564 A 9/2007
JP 04016441 B2 12/2007
JP 04022372 B2 12/2007
JP 2008018242 A 1/2008
JP 04051812 B2 2/2008
JP 04072721 B2 4/2008
JP 04077902 B2 4/2008
JP 04078245 B2 4/2008
JP 04084060 B2 4/2008
JP 04086185 B2 5/2008
JP 04108054 B2 6/2008
JP 04121709 B2 7/2008
JP 04163384 B2 10/2008
JP 04179634 B2 11/2008
JP 2008264586 A 11/2008
JP 04198986 B2 12/2008
JP 04209412 B2 1/2009
JP 2009090882 A 4/2009
JP 04279494 B2 6/2009
JP 04308723 B2 8/2009
JP 2009178570 A 8/2009
JP 2009254436 A 11/2009
JP 2009273214 A 11/2009
JP 04387106 B2 12/2009
JP 04391680 B2 12/2009
JP 04414925 B2 2/2010
JP 04440499 B2 3/2010
JP 04467187 B2 5/2010
JP 04468965 B2 5/2010
JP 04484320 B2 6/2010
JP 04512150 B2 7/2010
JP 2010158532 A 7/2010
JP 04523961 B2 8/2010
JP 04523962 B2 8/2010
JP 04548450 B2 9/2010
JP 04549407 B2 9/2010
JP 2010246941 A 11/2010
JP 04611364 B2 1/2011
JP 04611365 B2 1/2011
JP 04646393 B2 3/2011
JP 04655231 B2 3/2011
JP 04656332 B2 3/2011
JP 04674978 B2 4/2011
JP 2011072533 A 4/2011
JP 2011116765 A 6/2011
JP 04728351 B2 7/2011
JP 04741242 B2 8/2011
JP 04741489 B2 8/2011
JP 2011161401 A 8/2011
JP 04795536 B2 10/2011
JP 04851333 B2 1/2012
JP 04865825 B2 2/2012
JP 04881154 B2 2/2012
JP 04897811 B2 3/2012
JP 04907028 B2 3/2012
JP 04908737 B2 4/2012
JP 04964854 B2 7/2012
JP 04987999 B2 8/2012
JP 05047447 B2 10/2012
JP 05048749 B2 10/2012
JP 05093869 B2 12/2012
JP 05102033 B2 12/2012
JP 05164558 B2 3/2013
JP 05185629 B2 4/2013
JP 05193059 B2 5/2013
JP 05197636 B2 5/2013
JP 2013078564 A 5/2013
JP 05215580 B2 6/2013
JP 05267227 B2 8/2013
JP 05286268 B2 9/2013
JP 2013192711 A 9/2013
JP 2014004303 A 1/2014
JP 05427620 B2 2/2014
JP 05429714 B2 2/2014
JP 05440528 B2 3/2014
JP 05440529 B2 3/2014
JP 05461710 B2 4/2014
JP 05500348 B2 5/2014
JP 2014091049 A 5/2014
JP 2014114784 A 6/2014
JP 05539484 B2 7/2014
JP 05557175 B2 7/2014
JP 05590213 B2 9/2014
JP 05596974 B2 10/2014
JP 05611948 B2 10/2014
JP 05633512 B2 12/2014
JP 05656835 B2 1/2015
JP 05673795 B2 2/2015
JP 05675786 B2 2/2015
JP 05676118 B2 2/2015
JP 05701848 B2 4/2015
JP 05711245 B2 4/2015
JP 05750492 B2 7/2015
JP 05781597 B2 9/2015
JP 2015159947 A 9/2015
JP 05837162 B2 12/2015
JP 05868180 B2 2/2016
JP 05894116 B2 3/2016
JP 05894678 B2 3/2016
JP 2016028764 A 3/2016
JP 2016182342 A 10/2016
JP 06034858 B2 11/2016
JP 06038018 B2 12/2016
JP 06054106 B2 12/2016
JP 2016202553 A 12/2016
JP 06083929 B2 2/2017
JP 2017035323 A 2/2017
JP 2017517306 A 6/2017
JP 2017127675 A 7/2017
JP 06178666 B2 8/2017
JP 2017159083 A 9/2017
JP 06220867 B2 10/2017
JP 06236451 B2 11/2017
JP 06267625 B2 1/2018
JP 2018020199 A 2/2018
JP 06295204 B2 3/2018
JP 06329358 B2 5/2018
JP 06339371 B2 6/2018
JP 06345112 B2 6/2018
JP 06353787 B2 7/2018
JP 06382285 B2 8/2018
JP 2018122146 A 8/2018
JP 2018523541 A 8/2018
WO WO87/002894 A2 5/1987
WO WO88/009874 A1 12/1988
WO WO92/002263 A1 2/1992
WO WO92/003181 A1 3/1992
WO WO96/14027 A1 5/1995
WO WO95/031196 A1 11/1995
WO WO96/016684 A1 6/1996
WO WO98/042984 A1 10/1998
WO WO00/019097 A1 4/2000
WO WO00/027446 A1 5/2000
WO WO00/035515 A1 6/2000

(56) References Cited

FOREIGN PATENT DOCUMENTS

WO WO01/017581 A2 3/2001
WO WO01/019444 A1 3/2001
WO WO01/041070 A1 6/2001
WO WO01/074419 A1 10/2001
WO WO01/087176 A1 11/2001
WO WO01/095813 A1 12/2001
WO WO02/47751 A2 6/2002
WO WO02/053226 A2 7/2002
WO WO02/070039 A2 9/2002
WO WO02/072000 A1 9/2002
WO WO02/081021 A1 10/2002
WO WO03/024501 A2 3/2003
WO WO03/061727 A2 7/2003
WO WO03/094716 A1 11/2003
WO WO03/103745 A2 12/2003
WO WO2004/026394 A1 4/2004
WO WO2004/034034 A1 4/2004
WO WO2004/088480 A2 10/2004
WO WO2004/098677 A1 11/2004
WO WO2005/020848 A2 3/2005
WO WO2005/033671 A1 4/2005
WO WO2005/037348 A1 4/2005
WO WO2005/054680 A1 6/2005
WO WO2005/108796 A1 11/2005
WO WO2006/040252 A1 4/2006
WO WO2006/053384 A1 5/2006
WO WO2006/081255 A2 8/2006
WO WO2006/121698 A2 11/2006
WO WO2007/008907 A2 1/2007
WO WO2007/033933 A1 3/2007
WO WO2007/053881 A1 5/2007
WO WO2007/065408 A2 6/2007
WO WO2007/092494 A2 8/2007
WO WO2007/105842 A1 9/2007
WO WO2007/146231 A2 12/2007
WO WO2008/005747 A2 1/2008
WO WO2008/008427 A2 1/2008
WO WO2008/088874 A2 7/2008
WO WO2008/102015 A1 8/2008
WO WO2008/121143 A1 10/2008
WO WO2008/121145 A1 10/2008
WO WO2008/137237 A2 11/2008
WO WO2008/140034 A1 11/2008
WO WO2009/017549 A1 2/2009
WO WO2009035581 A1 3/2009
WO WO2009/046789 A1 4/2009
WO WO2009/075668 A2 6/2009
WO WO2009/096991 A1 8/2009
WO WO2010/025411 A2 3/2010
WO WO2010/119110 A1 10/2010
WO WO2011/003043 A1 1/2011
WO WO2011/024928 A1 3/2011
WO WO2011/035925 A1 3/2011
WO WO2011/039091 A1 4/2011
WO WO2011/081629 A1 7/2011
WO WO2011/082212 A1 7/2011
WO WO2011/085040 A1 7/2011
WO WO2011/117566 A1 9/2011
WO WO2011/119060 A2 9/2011
WO WO2012/037506 A2 3/2012
WO WO2012/051454 A2 4/2012
WO WO2012/064674 A1 5/2012
WO WO2012/075152 A1 6/2012
WO WO2012/075262 A1 6/2012
WO WO2012/087811 A2 6/2012
WO WO2012/094535 A2 7/2012
WO WO2012/094641 A2 7/2012
WO WO2012/096716 A2 7/2012
WO WO2012/112129 A1 8/2012
WO WO2013/034547 A1 3/2013
WO WO2013/093058 A1 6/2013
WO WO2013/127182 A1 9/2013
WO WO2013/134319 A1 9/2013
WO WO2013/148560 A1 10/2013
WO WO2013/148697 A1 10/2013
WO WO2014/070458 A1 5/2014
WO WO2014/096408 A1 6/2014
WO WO2014/106635 A1 7/2014
WO WO2014/116639 A1 7/2014
WO WO2014/142754 A1 9/2014
WO WO2014/143593 A1 9/2014
WO WO2014/164136 A1 10/2014
WO WO2014/164292 A1 10/2014
WO WO2014/166128 A1 10/2014
WO WO2014/169023 A2 10/2014
WO WO2015/119705 A1 8/2015
WO WO2015/160943 A1 10/2015
WO WO2015/160979 A1 10/2015
WO WO2015/171156 A1 11/2015
WO WO2015/175711 A1 11/2015
WO WO2015/175718 A1 11/2015
WO WO2015/177793 A2 11/2015
WO WO2015/187659 A2 12/2015
WO WO2016/100600 A2 6/2016
WO WO2016/113266 A1 7/2016
WO WO2016/116630 A2 7/2016
WO WO2017/001358 A1 1/2017
WO WO2017/011257 A1 1/2017
WO WO2017/032751 A1 3/2017
WO WO2017/048733 A1 3/2017
WO WO2017/060254 A1 4/2017
WO WO2017/060257 A1 4/2017
WO WO2017/075322 A1 5/2017
WO WO2017/087380 A1 5/2017
WO WO2017/120453 A1 7/2017
WO WO2017/133425 A1 8/2017
WO WO2017/134657 A1 8/2017
WO WO2017/139113 A1 8/2017
WO WO2017/139246 A1 8/2017
WO WO2017/147082 A1 8/2017
WO WO2017/147103 A1 8/2017
WO WO2017/147291 A1 8/2017
WO WO2017/151987 A1 9/2017
WO WO2017/156386 A1 9/2017
WO WO2017/159849 A1 9/2017
WO WO2017/165372 A1 9/2017
WO WO2017/178904 A1 10/2017
WO WO2017/183124 A1 10/2017
WO WO2017/190155 A2 11/2017
WO WO2017/192119 A1 11/2017
WO WO2017/196271 A1 11/2017
WO WO2017/205909 A1 12/2017
WO WO2017/210318 A2 12/2017
WO WO2017/214118 A1 12/2017
WO WO2017/214183 A1 12/2017
WO WO2017/217946 A1 12/2017
WO WO2018/007120 A1 1/2018
WO WO2018/007471 A1 1/2018
WO WO2018/017678 A1 1/2018
WO WO2018/017683 A1 1/2018
WO WO2018/017716 A1 1/2018
WO WO2018/026764 A1 2/2018
WO WO2018/026769 A1 2/2018
WO WO2018/031741 A1 2/2018
WO WO2018/035069 A1 2/2018
WO WO2018/039124 A1 3/2018
WO WO2018/039326 A1 3/2018
WO WO2018/041963 A1 3/2018
WO WO2018/045299 A1 3/2018
WO WO2018/051091 A1 3/2018
WO WO2018/052482 A1 3/2018
WO WO2018/057482 A1 3/2018
WO WO2018/057563 A1 3/2018
WO WO2018/061002 A1 4/2018
WO WO2018/064437 A1 4/2018
WO WO2018/067410 A1 4/2018
WO WO2018/073150 A1 4/2018
WO WO2018/078370 A1 5/2018
WO WO2018/078615 A1 5/2018
WO WO2018/082987 A1 5/2018
WO WO2018/088939 A1 5/2018
WO WO2018/089970 A1 5/2018
WO WO2018/093663 A1 5/2018
WO WO2018/096531 A1 5/2018

(56) References Cited

FOREIGN PATENT DOCUMENTS

| | | | |
|---|---|---|---|
| WO | WO2018/118756 | A1 | 6/2018 |
| WO | WO2018/132181 | A1 | 7/2018 |
| WO | WO2018/132182 | A1 | 7/2018 |
| WO | WO2018/135477 | A1 | 7/2018 |
| WO | WO2018/135478 | A1 | 7/2018 |
| WO | WO2018/136592 | A2 | 7/2018 |
| WO | WO2018/139508 | A1 | 8/2018 |
| WO | WO2018/145434 | A1 | 8/2018 |
| WO | WO2018/146045 | A1 | 8/2018 |
| WO | WO2018/146170 | A1 | 8/2018 |
| WO | WO2018/146173 | A1 | 8/2018 |
| WO | WO2018/146177 | A1 | 8/2018 |
| WO | WO2018/148456 | A1 | 8/2018 |
| WO | WO2018/156524 | A1 | 8/2018 |
| WO | WO2018/158636 | A1 | 9/2018 |
| WO | WO2018/177344 | A1 | 10/2018 |
| WO | WO2018/178939 | A1 | 10/2018 |
| WO | WO2018/183128 | A1 | 10/2018 |
| WO | WO2018/187576 | A2 | 10/2018 |
| WO | WO2018/226991 | A1 | 12/2018 |
| WO | WO2019/094963 | A1 | 5/2019 |
| WO | WO2019/138350 | A2 | 7/2019 |
| WO | WO2019/158996 | A1 | 8/2019 |
| WO | WO2019/191851 | A1 | 9/2019 |
| WO | WO2019/194956 | A1 | 10/2019 |
| WO | WO2019/229222 | A1 | 12/2019 |
| WO | WO2020/028537 | A1 | 2/2020 |
| WO | WO2020/0234785 | A1 | 11/2020 |
| WO | WO2021/026469 | A1 | 2/2021 |
| WO | WO2021/026472 | A1 | 2/2021 |
| WO | WO2021/062260 | A1 | 4/2021 |
| WO | WO2021/062265 | A1 | 4/2021 |
| WO | WO2021/062270 | A1 | 4/2021 |
| WO | WO2021/119478 | A1 | 6/2021 |
| WO | WO2021/127503 | A1 | 6/2021 |
| WO | WO2021/152019 | A1 | 8/2021 |
| WO | WO2021/158967 | A1 | 8/2021 |
| WO | WO2021/195617 | A1 | 9/2021 |
| WO | WO2021/222403 | A1 | 11/2021 |
| WO | WO2021/231574 | A1 | 11/2021 |
| WO | WO2021/243263 | A1 | 12/2021 |
| WO | WO2022/072944 | A1 | 4/2022 |
| WO | WO2022/076862 | A1 | 4/2022 |
| WO | WO2022/076948 | A1 | 4/2022 |
| WO | WO2022/120270 | A1 | 6/2022 |
| WO | WO2022/173970 | A1 | 8/2022 |
| WO | WO2022/187747 | A1 | 9/2022 |
| WO | WO2022/204400 | A1 | 9/2022 |
| WO | WO2022/216794 | A1 | 10/2022 |
| WO | WO2022/216799 | A1 | 10/2022 |

OTHER PUBLICATIONS

Jagani et al.; Dual-propeller cavopulmonary pump for assisting patients with hypoplastic right ventricle; ASAIO Joumal (American Society for Artificial Internal Organs); 10 pages; DOI: 10.1097/MAT.0000000000000907; Jan. 2019.

Park et al.; Biologically Inspired, Open, Helicoid Impeller Design for Mechanical Circulatory Assist; ASAIO Journal (American Society for Artificial Internal Organs); DOI: 10.1097/MAT.0000000000001090; Oct. 23, 2019.

Reitan et al.; First human use of the reitan catheter pump; Asaio Journal; 47(2); p. 124; Mar.-Apr. 2001.

Gupta et al.; U.S. Appl. No. 29/761,852 entitled "Intravascular blood pump external display screen or a portion thereof with graphical user interface," filed Dec. 11, 2020.

Varghai et al.;U.S. Appl. No. 17/794,002 entitled "Intravascular blood pumps, motors, and fluid control," filed Jul. 20, 2022.

Hildebrand et al., U.S. Appl. No. 17/907,321 entitled "Intravascular blood pumps," filed Sep. 26, 2022.

Salahieh et al.; U.S. Appl. No. 18/047,076 entitled "Intravascular fluid movement devices, systems, and methods of use," filed Oct. 17, 2022.

Saul et al.; U.S. Appl. No. 17/998,614 entitled "Inflatable medical devices, methods of manufacture and use," filed Nov. 11, 2022.

Ryan et al.; U.S. Appl. No. 17/998,624 entitled "Catheter blood pumps and collapsible pump housings," filed 111/Nov. 2022.

Calomeni et al.; U.S. Appl. No. 18/614,131 entitled "Intravascular blood pumps and methods of manufacture and use," filed Mar. 22, 2024.

Brandt et al.; U.S. Appl. No. 18/554,756 entitled "Catheter blood pump shrouds and assembly thereof," filed Oct. 10, 2023.

Ryan et al.; U.S. Appl. No. 18/559,231 entitled "Intravascular blood pump outflow flow disruptor," filed Nov. 6, 2023.

Salahieh et al.; U.S. Appl. No. 18/615,896 entitled "Intravascular blood pumps and methods of use and manufacture," filed Mar. 25, 2024.

Varghai et al.; U.S. Appl. No. 18/711,528 entitled "Intravascular blood pumps, motors, and fluid control," filed May 17, 2024.

Hildebrand; U.S. Appl. No. 18/710,551 entitled "Intravascular blood pumps and expandable scaffolds with stiffening members" filed May 15, 2024.

* cited by examiner

Figure 11

INTRAVASCULAR BLOOD PUMPS AND CONTROL THEREOF

CROSS REFERENCE TO RELATED APPLICATIONS

This application claims priority to U.S. Provisional Application No. 63/016,667, filed Apr. 28, 2020, the disclosure of which is incorporated by reference herein for all purposes.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Medical devices may be adapted to be coupled to an external console, wherein the external console is configured to monitor and/or control one or more aspects of the medical device. For example, without limitation, intravascular blood pumps may be adapted to be coupled to an external console, with the external console monitoring and/or controlling one or more aspects of the use of the external console and/or the intravascular blood pump.

Software and/or firmware on the external console may monitor and/or control one or more aspects of the external console and/or the intravascular blood pump. It may be suboptimal for the software and/or firmware on the external console to be under the control of one or more aspects of the external console, such as a console operating system ("OS"). For example, without limitation, if a console OS stops performing optimally or ceases to function altogether, software, firmware, and/or hardware within the external console that may be monitoring and/or controlling one or more aspects of the external console and/or the intravascular blood pump may not function properly or may stop functioning altogether. In some instances, the software and/or firmware on the external console may be unable to detect if hardware on the external console is not performing correctly, consequences of which may be severe or even life threatening depending on the particular application. Additionally, it may be desirable to have more control over software and/or firmware used with an intravascular blood pump (including development thereof) than if it is under the control of a third-party OS.

SUMMARY OF THE DISCLOSURE

Some aspects of this disclosure provide risk mitigation for intravascular blood pumps. In some embodiments the mitigation includes providing an alert or notification (manual and/or automatic) when one or more aspects of an external console is not performing optimally or has stopped performing altogether. In some particular but exemplary embodiments, an intravascular blood pump includes a controller that is adapted to cause an output to be provided if information indicative of a sensed characteristic of fluid in a fluid pathway indicates that one or more aspects of an external console are not performing as expected. For example only, if an operating system on an external console were to stop performing optimally or stop performing altogether (e.g., an OS crash), software and/or hardware used with the intravascular blood pump that is controlled by the OS may stop functioning properly, the consequences of which may be severe, perhaps even life-threatening. In some embodiments, a controller disposed within the intravascular blood pump may be adapted to receive information and initiate an output if the information is indicative that one or more aspects of the console are not performing as expected for any number of reasons. The received information may be, in some embodiments, information indicative of a sensed characteristic of fluid in at least a portion of a purge fluid pathway, such as in at least a portion of a clean purge fluid pathway and/or a purge fluid return pathway. In some embodiments, the received information may be indicative of fluid pressure and/or fluid flow. In some merely exemplary embodiments, the received information may be indicative that hardware on an external console is not performing or being controlled correctly. In some merely exemplary embodiments, external hardware that may not be performing or controlled correctly may be a fluid controller (e.g., a fluid pump, such as a peristaltic pump) for controlling the flow of fluid (e.g., purge fluid and/or sheath fluid). A portion of a clean purge fluid pathway may extend through at least a portion of the intravascular blood pump. A portion of a return purge fluid pathway may extend through at least a portion of the intravascular blood pump.

In some embodiments, the controller may include a control unit disposed within an intravascular blood pump (e.g., within a handle of the blood pump), wherein the intravascular blood pump is adapted to be coupled to an external console to put the external console and the intravascular blood pump in operable communication (e.g., one or more of electrical communication, mechanical communication, and/or fluid communication (e.g., liquid and/or gas).

In some merely exemplary embodiments, the controller may be adapted to cause an output to be provided (e.g., on the handle or on the external console) if there is an indication that, based on input information, a fluid controller in an external console may not be functioning properly. The fluid controller may be a fluid control that is adapted and positioned to control one or more aspects of a fluid that is being pumped into the intravascular blood pump, such as purge fluid and/or fluid pumped through an outer sheath of the intravascular blood pump. In some merely exemplary embodiments, the fluid controller may be a fluid pump that is adapted to cause fluid to move through a purge fluid pathway.

Some aspects of this disclosure may be related to maintaining fluid flow through one or more fluid flow paths. In some implementations, these aspects may include maintaining purge fluid pressure at one or more fluid flow locations.

BRIEF DESCRIPTION OF THE DRAWINGS

FIG. 11 illustrates a merely exemplary sequence of steps that may be part of computer executable methods herein.

DETAILED DESCRIPTION

Figure 1:
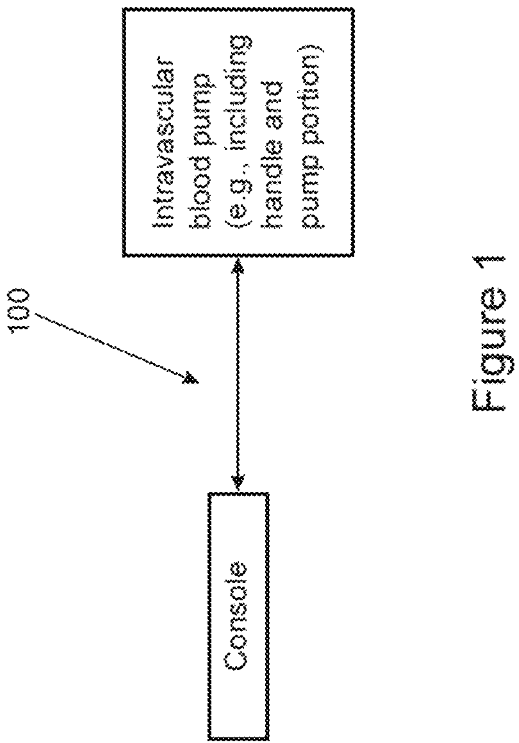
FIG. 1 schematically illustrates an external console, which may be part of an external console assembly, coupled to an intravascular blood pump or catheter assembly.

FIG. 1 schematically illustrates an external console assembly in operative communication with an intravascular catheter blood pump, which may optionally include a handle portion, a catheter portion, and a pump portion. Communication 100 can include one or more of electrical communication, fluid communication, or mechanical communication, any of which may be one way or two-way communication.

In some embodiments, risk mitigation may be accomplished by performing one or more actions with the intravascular blood pump. For example, without limitation, a controller or control unit disposed in, on, or otherwise carried by the intravascular blood pump (e.g., within a handle portion thereof) may be configured to receive information and perform one or more actions or events in response to the received information. A controller herein may comprise any number of software and/or hardware components alone or together that are associated with one or more components of the intravascular blood pump.

An exemplary benefit of exemplary systems herein in which one or more aspects of system monitoring or control are not under direct control of software or firmware controlling the external console (e.g., not controlled by an OS on the console) is that it is possible for the system to be able check or verify that the one or more aspects of the system are functioning properly when a part of the system that controls the aspect has stopped performing optimally or stopped functioning altogether (e.g., an OS on the console crashes). This may generally be referred to herein as being adapted to provide risk mitigation. For example, if software on the console (e.g., an OS) stops functioning, it may prevent one or more applications stored on the console from functioning. In some particular embodiments, an application on the console may be in control of hardware associated with the console (e.g., a peristaltic pump(s), a flow regulator(s), a valve), and if the console cannot control the application, the console may be unable to control the hardware on the console. Additionally, it may not be apparent to a user that control of the system component has stopped or become intermittent, which may create a serious risk to the patient's health. Some aspects of the systems herein provide risk mitigation by providing a different part of the system that can initiate (or cause) an output if there is an indication that part of the system is not performing as intended. There are a variety of ways in which to implement the risk mitigating functionality described herein.

Figure 2:
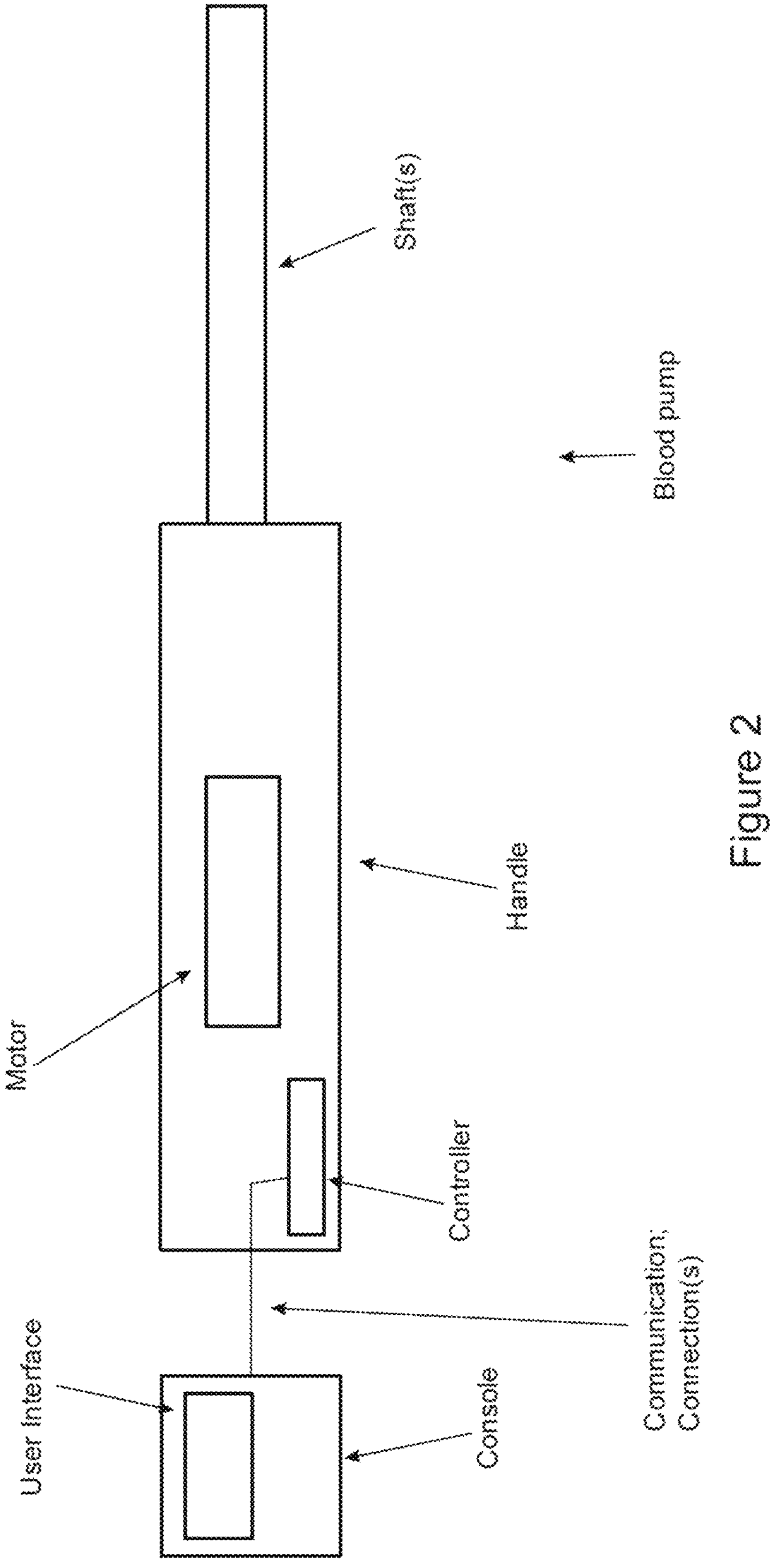
FIG. 2 schematically illustrates an external console, which may be part of an external console assembly, coupled to an intravascular blood pump or catheter assembly that includes a handle portion with a controller.

FIG. 2 schematically illustrates an exemplary embodiment of an intravascular blood pump system that is adapted to provide risk mitigation. A system in this context refers to an intravascular blood pump and one or more external components (such as an external console assembly), where the intravascular blood pump is adapted to be coupled with the one or more external components. In the exemplary system illustrated schematically in FIG. 2, the blood pump includes a controller (e.g., a microcontroller), which in this embodiment is within a handle portion of the blood pump as shown. The handle portion also includes a motor therein that is in rotational operation with one or more impellers in the pump portion (pump portion not shown for clarity). The shaft as shown is generally considered a catheter portion of the catheter assembly, and extends between handle portion and the pump portion. The controller may be in electrical communication with the external console assembly via the communication/connection(s) shown. The communication may be one-way (either direction) or two-way, and may include any number of lines. The catheter assembly controller may also be in communication with the motor. The external console assemblies herein may include a console that may include a user interface (e.g., including a touchscreen) that can allow for input to the console and/or is adapted to provide a variety of outputs to the user interface. The system shown schematically in FIG. 2 may include any other suitable components of any other system herein.

Figure 3:
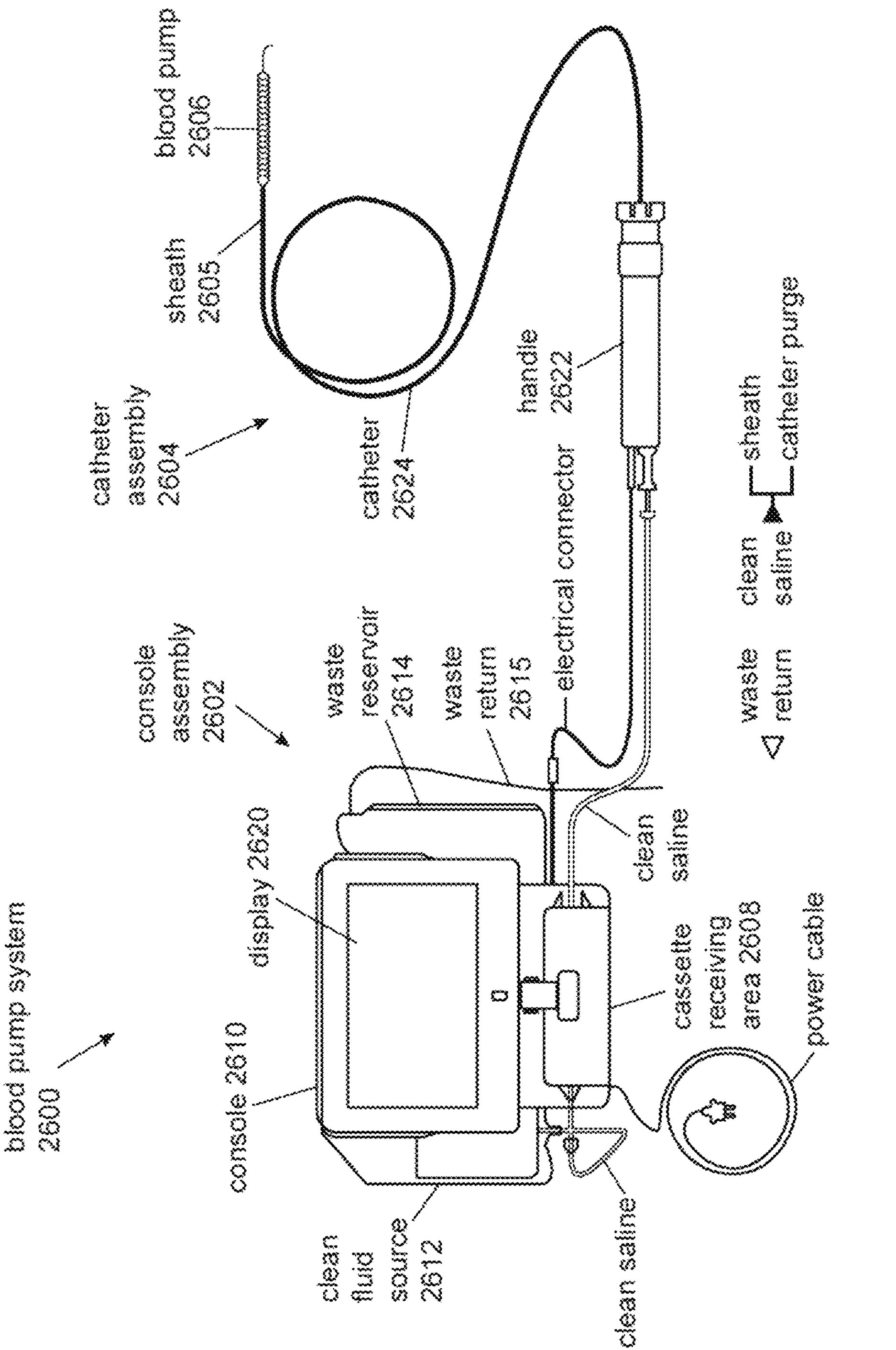
FIG. 3 illustrates an exemplary intravascular blood pump system, wherein a catheter assembly is coupled to an external console assembly.

FIG. 3 illustrates an exemplary intravascular blood pump system that includes an external console assembly that is adapted and configured to be in operative communication with a catheter assembly, which includes a pump portion that is configured to move blood. FIG. 3 schematically illustrates an exemplary intravascular blood pump system 2600, which includes an external console assembly 2602 and a catheter assembly 2604, which are both configured to be coupled with one another and placed in operative communication. The catheter assembly 2604 includes a catheter portion 2624 and a handle portion 2622 at a proximal portion of the catheter portion 2624 and a blood pump or pump portion 2606 at a distal portion of the catheter portion 2624. The blood pump 2606 is adapted to be placed within a patient's body and the handle portion 2622 is spaced to remain outside of the patient. The handle portion 2622 may include one or more motors for driving the rotation of one or more impellers of blood pump 2606. The catheter assembly 2604 is adapted to be coupled to and placed into electrical and fluidic communication with console assembly 2602. The console 2610 may include one or more pumps (e.g., peristaltic pumps) to provide fluidic flow to the catheter 2624, and a controller (e.g., an OS, software) thereon configured to control the operation of the pump(s) to thereby control the fluid flow to the catheter. The console 2610 generally includes a user interface, including a display (e.g., touch display) for displaying and/or inputting information related to operation of the blood pump system, such as the console assembly 2602 and/or catheter assembly 2604. The console may also include a cassette receiving area 2608 that is configured to receive a removable fluid cassette that is adapted to facilitate fluid delivery (e.g., clean saline) from a clean fluid source 2612 (e.g., saline bag) into one or more fluid pathways, such a first fluidic pathway (e.g., catheter fluidic pathway) and a second fluidic pathway (e.g., sheath fluidic pathway). A catheter fluid pathway may be used to provide fluid from the console assembly 2602 through the catheter portion 2624, and a sheath fluidic pathway may be used to provide fluid from the console assembly 2602 to the space between an axially movable outer sheath 2605 and an outer surface of a catheter portion shaft. A waste fluid return line 2615 may be used to return waste fluid from the catheter assembly 2604 to a waste reservoir 2614 (e.g., a waste bag). In some cases, the waste reservoir 2614 is coupled to the console 2610. In some examples, the console 2610 includes one or more scales near the clean fluid source 2612 and/or the waste reservoir 2614 that are used to measure the weight of the clean fluid source 2612 and/or the waste reservoir 2614.

Figures 4A, 4B:
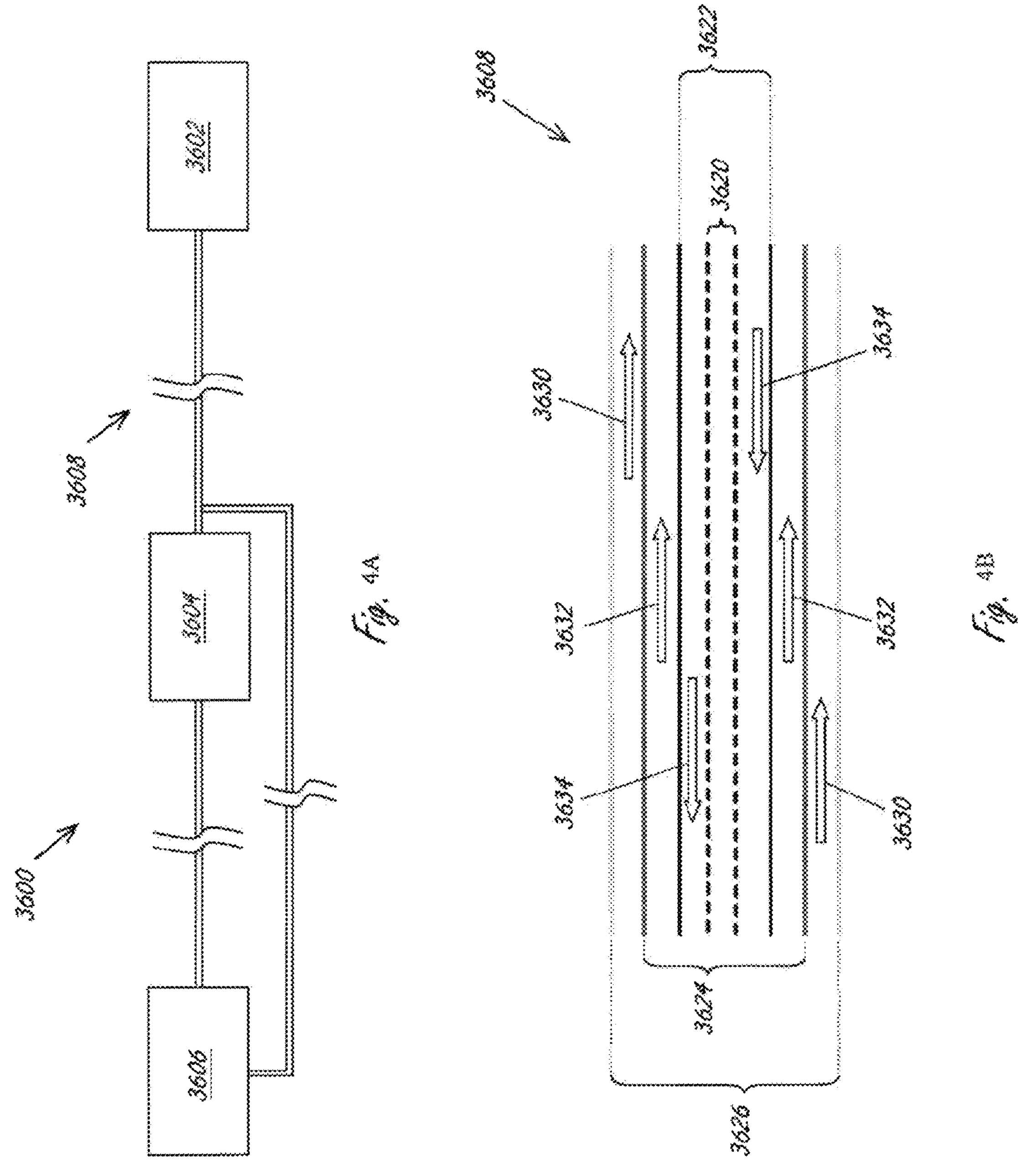
FIG. 4A schematically illustrates an exemplary blood pump system.
FIG. 4B illustrates exemplary fluid pathways of an exemplary intravascular blood pump.

FIG. 4A schematically illustrates at least a portion of an exemplary blood pump system 3600. Any of the blood pump systems described herein may have the arrangement of system 3600. The exemplary blood pump system 3600 may include an optional external console assembly 3606 and a catheter assembly 3608, which may include catheter portion 3604 and pump portion 3602. Catheter portion 3604 in this example may also include a handle portion, such as any of the handle portions herein. Console assembly 3606 may include one or more controllers (e.g., an operating system and/or software) for controlling aspects of the external console assembly and/or a motor that is used to rotate one or more impellers of blood pump 3602. Console assembly 3606 may be in fluid and/or electrical communication with a motor assembly of the catheter assembly via, for example, one or more electrical wires and/or one or more fluidic channels. In some examples, the console assembly 3606 may be in fluid and/or electrical communication with the catheter assembly 3608 via, for example, one or more electrical wires and/or one or more fluidic channels (e.g., bypassing the motor assembly 3604).

FIG. 4B schematically illustrates an exemplary sectional view (distal to the right, proximal to the left) of at least a portion of an exemplary catheter assembly 3608, and illustrates exemplary and optional fluid pathways therein, which may be part of any of the catheter portions herein. The catheter assembly 3608 may include a plurality of coaxial tubular components including a hollow driveshaft 3620, a driveshaft tube 3622, a catheter shaft 3624 and an outer sheath 3626. The hollow driveshaft 3620 may be in rotational communication with one or more impellers of a pump portion of the blood pump 3602. The hollow driveshaft 3620 may be configured to rotate by being rotatably coupled to a motor of the system. The hollow driveshaft 3620 may include or define an inner lumen to accommodate, for example, a guidewire. The driveshaft tube 3622 may be sized and configured to house therein the rotatable driveshaft 3620. The catheter shaft 3624 (which may be referred to simply as a catheter, and which may include one or more layers of material) may be considered an outermost tubular member of the catheter portion along a substantially length of the catheter portion. A catheter shaft may house components of the blood pump 3602 at a distal portion of the catheter 3624, such as one or more bearing assemblies of the blood pump 3602. Once, in position, sheath 3626 may be retracted proximally to optionally allow expansion of the optionally expandable portions of the blood pump 3602. A motor assembly may be generally adapted to rotate the driveshaft 3620.

Depending on the particular design of the catheter portion, the catheter portion may include one or more fluid pathways to facilitate fluid flow in and through one or more annular spaces between components of the catheter portion 3608. For example, clean fluid (e.g., clean saline) may flow (e.g., by being pumped with a pump in the external console assembly) toward the blood pump 3602 via a sheath fluid pathway 3630 between the sheath 3626 and an outer surface of catheter shaft 3624. Fluid flow through the sheath fluid pathway 3630 may prevent blood from stagnating and forming clots in the annular space between the sheath 3626 and the catheter shaft 3624 at a distal end of the sheath 3626. Fluid from the sheath fluid pathway 3630 may enter the patient's body with no substantial return fluid pathway. Clean purge fluid (e.g., saline pumped from a saline bag disposed outside the patient) may also flow (e.g., by being pumped) toward the blood pump 3602 via a catheter clean fluid pathway 3632 between the catheter shaft 3624 and the driveshaft tube 3622. Some or all of the fluid in the catheter clean fluid pathway 3632 may return from the blood pump 3602 via a return fluid pathway 3634 (which may be referred to in any embodiment herein as a waste fluid pathway). Flowing fluid through the catheter fluid pathway 3632 and return fluid pathway 3634 may cool and/or lubricate moving components (e.g., the rotating driveshaft 3620 and bearings) within the blood pump 3602. The catheter clean fluid pathway 3632 and return fluid pathway 3634 may flush and keep possible debris (e.g., from wear of rotating components) from entering the patient's body. In some examples, where a wall of the driveshaft 3620 has some porosity, fluid within the return fluid pathway 3634 may passively enter the inner lumen of the driveshaft 3620.

In any of the embodiments herein, a driveshaft, a driveshaft tube, a catheter shaft and optionally an outer sheath may all be co-axial.

Optionally, clean fluid for the sheath fluid pathway 3630 and the catheter fluid pathway 3632 may be provided by a console 3606, which may include one or more clean fluid sources (e.g., saline bags) and a pump assembly (e.g., peristaltic pump assembly) for moving clean fluid distally toward the blood pump 3602. In some examples, the clean fluid may be provided to the catheter portion 3608 through a catheter fluid inlet and a sheath fluid inlet between the motor assembly 3604 and the blood pump 3602. In some cases, one or both of the catheter fluid inlet and the sheath fluid inlet are part of (or connected to) the motor assembly 3604. In some examples, the return fluid pathway 3634 may flow through a motor assembly (not shown) and toward a waste reservoir, which optionally may be connected to (or part of) such as by being secured to, a console assembly.

Any controller or control unit herein (e.g., the controller shown in FIG. 4) may include one or more of a microcontroller, hardware, software or firmware, for example.

In some particular exemplary embodiments, the blood pump systems are adapted with risk mitigation functionality to detect if one or more aspects of the console is not performing as intended. For example, some systems may be adapted to determine if fluid (e.g., clean fluid, return fluid, sheath fluid) is not flowing in a fluid pathway as intended or desired, or there is otherwise some problem with the fluid pathway. In some embodiments, the system is adapted to create or cause an output or alert or notification if fluid is not being controlled in a desired or intended manner. For example without limitation, some systems may include a fluid return pathway from the intravascular blood pump, the pathway including one or more fluid lines. An exemplary fluid pathway may be a purge fluid return pathway or a clean purge pathway, and in the case of a return pathway, at least a portion of purge fluid that is delivered to the blood pump moves away from the blood pump after passing through at least a portion of the blood pump. By way of example only, a system may include or more features that are adapted to modify flow in a fluid pathway, such as from switching from fluid flow to no fluid flow. Exemplary features in this regard include software on the console and/or hardware on the console such as a peristaltic pump.

In an exemplary implementation of FIG. 2 or 3, the console assembly may include one or more fluid flow regulators (e.g., one or more peristaltic pumps, valves, etc.) that are adapted to be controlled by software/firmware stored on the console, such as a console operating system. If the console fluid flow regulator can no longer be effectively controlled, firmware/software on the blood pump controller is adapted to be part of a detection and/or notification process that some aspect of the external console (e.g., a flow regulator) has stopped functioning properly, optionally due to a console operating system malfunction. The process may include causing an alert, notification, or otherwise provide an indication of an event that is indicative of the decrease in functionality. An exemplary alert may occur on the console or a blood pump handle portion, for example.

In some embodiments of the system, one or more sensors (e.g., pressure sensors, flow sensors) are in communication (directly or indirectly) with the blood pump controller. For example, without limitation, the controller may be in communication with one or more sensors that provide information indicative of one or more sensed characteristics of fluid in a fluid pathway extending from the handle (such as any of the pathways shown in FIG. 4B). The fluid pathway may be one or more of a clean fluid pathway, a return fluid pathway, or a sheath fluid pathway. Any of these sensors may be disposed in or carried by any suitable portion of the intravascular blood pump system, such as within an external console fluid pathway, within a fluid pathway within the handle portion, within a fluid pathway in a component removable from the console (e.g., a cassette), within a fluid pathway axially between the external console and the handle portion, within a fluid pathway in a catheter assembly or pump portion that is distal to a handle portion, etc. The one or more sensors may include a sensor adapted to sense flow along the fluid pathway, a sensor adapted to sense pressure along the fluid pathway, or both (and any number of each). Additionally, there may be sensors at a plurality of locations along any of the different fluid pathways herein that are adapted to sense information at the plurality of locations. For example, without limitation, an external console assembly (including a removable component such as a cassette) may include one or more pressure or flow sensors adapted to sense information indicative of one or more of fluid pressure or a flow rate in any of the fluid pathways herein.

Figure 5:
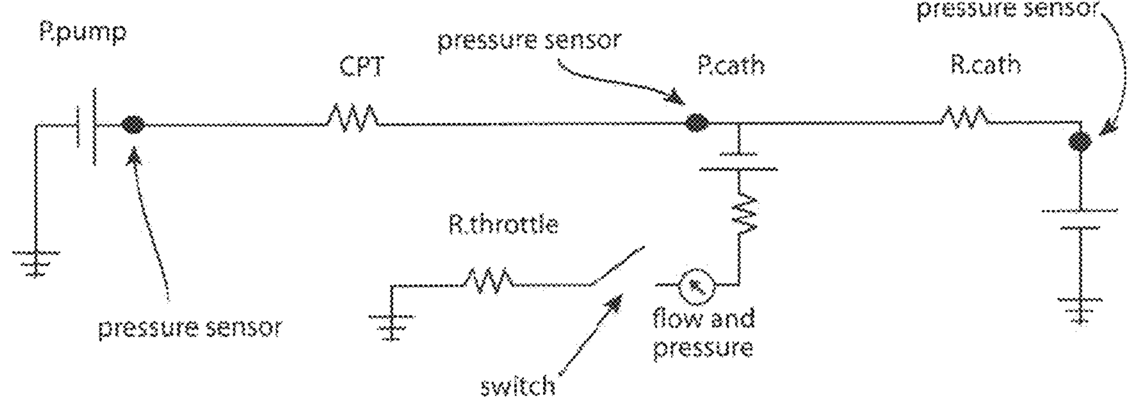
FIG. 5 provides a merely illustrative schematic representation of an exemplary blood pump system, including optional locations for optional pressure sensors.

FIG. 5 provides a merely illustrative schematic representation of an exemplary blood pump system, which may include an external console assembly that includes a flow regulator (e.g., a peristaltic pump—"P.pump"). Components are represented electrically to illustrate concepts, additional disclosure of which can be found herein.

Figure 6:
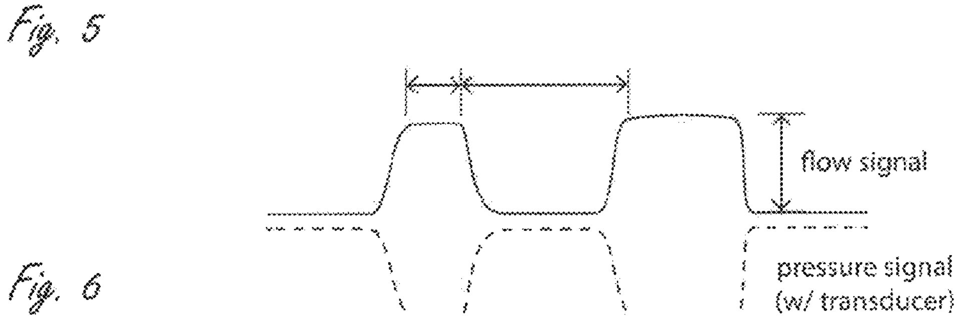
FIG. 6 provides exemplary flow and pressure waveforms, one or more aspects of which (e.g., a waveform, an amplitude, a temporal aspect) may be utilized according to any risk mitigation process or system herein.

In some implementations, the blood pump system may be adapted to cause or initiate an output when received information indicates that one or more sensed characteristics of fluid in a fluid path (e.g., clean purge fluid, return fluid, sheath fluid, etc.) is indicative of a fluid path flow regulator that is not functioning properly. Malfunctioning as described here may be due to hardware error, such as a pump that is no longer working and/or a software error, such as a console operating system error. In some implementations, the system is adapted to create an output (e.g., an output from an algorithm) if an aspect of flow in a fluid pathway is not, or diverges from, an expected aspect of the flow. In some implementations, the system is adapted to create an output if an aspect of flow changes from a current state to a different state. Fluid flows aspects, or characteristics, that may be indicative of a problem include information indicative of, but are not limited to, a flow rate amplitude (an example of which is shown in FIG. 6), a flow rate waveform (an example of which is shown in FIG. 6), a temporal aspect of flow, etc. Exemplary temporal aspects of flow include, but are not limited to, duration and/or timing of an expected phase, such as expected duration of a flow path being open and/or closed; duration and/or timing of an expected flow rate amplitude. The exemplary flow waveform shown in FIG. 6 illustrates by way of illustration and example only flow characteristics that may be utilized. In the flow signal waveform shown, the vertical arrows generally indicate signal amplitude. The horizontal arrows each illustrate exemplary duration (time) of different phases, with the leftmost arrow indicating the duration/time of a relatively higher flow phase, such as if a flow regulator (e.g., valve) allows return fluid to flow, whereas the horizontal arrow on the right could indicate the duration/time of a phase in which flow decreases, which could indicate a flow decrease, or is stopped altogether (e.g., flow regulator closes the flow path).

In exemplary particular risk mitigation implementations, the system may alternatively or in addition to, be adapted to cause or create an output (e.g., from an algorithm) if an aspect of fluid pressure in one or more fluid pathways (e.g., purge fluid return) is not, or diverges from, an expected aspect (e.g., stored in memory) of the flow. In some implementations, the system is adapted to create an output if an aspect of fluid pressure changes from a current state to a different state. Fluid pressure aspects, or characteristics, that may be indicative of a problem include information indicative of, but are not limited to, a pressure amplitude (e.g., as shown in FIG. 6 in dotted line), a pressure waveform (e.g., as shown in FIG. 6), a temporal aspect of pressure, etc. Temporal aspects of pressure include, but are not limited to, duration and/or timing of an expected phase, such as expected duration of pressure to be at or near a known amplitude. The exemplary pressure waveform in FIG. 6 illustrates by way of illustration and example only pressure characteristics that may be utilized. In the pressure waveform, the amplitude is represented vertically. The adjacent horizontal arrows each illustrate exemplary duration (time) of different phases, with the leftmost arrow indicating the duration/time of a relatively lower pressure, such as if a flow regulator (e.g., valve) allows return fluid to flow, whereas the horizontal arrow on the right could indicate the duration/time of a phase in which flow increases, which could indicate a fluid pressure increase (e.g., flow regulator closes a return fluid flow path). Alternatively, a sensed pressure may indicate if one or more fluid pumps in the console are operating properly. For example, if a fluid pressure drops, it may indicate that a fluid pump in the console is not functioning properly. Additionally, if a fluid pressure is outside of an acceptable range, it may indicate that a fluid pump (e.g., a peristaltic pump) in the console is not functioning properly.

An exemplary additional advantage of some of the methods herein that receive information indicative of sensed information is that the methods may ease the burden on accuracy requirements of one or more sensors. For example, the methods herein can be adapted to determine if sensed signals are within an expected window, which may be easier to implement than if looking for sensed signals at more discrete values.

Any of the characteristics of fluid herein (which includes information that is indicative of the fluid characteristics), such as fluid flow characteristics and fluid pressure characteristics may be stored in one or more system memory units that are outside of the direct control of the external console. In some implementations, the stored characteristics may be stored in a blood pump controller, such as the controller associated with the blood pump handle shown in FIGS. 1 and 2. Any of the fluid characteristics herein may be referred to herein as any of the following: stored characteristics, desired characteristics, expected characteristics, or other similar phrases or derivatives thereof.

The exemplary ways in which the systems herein are adapted to determine if one or more aspects of fluid are not, or if they diverge from, an expected aspect of fluid flow or fluid pressure are exemplary and do not limit the general concepts and processes herein.

Figure 9:
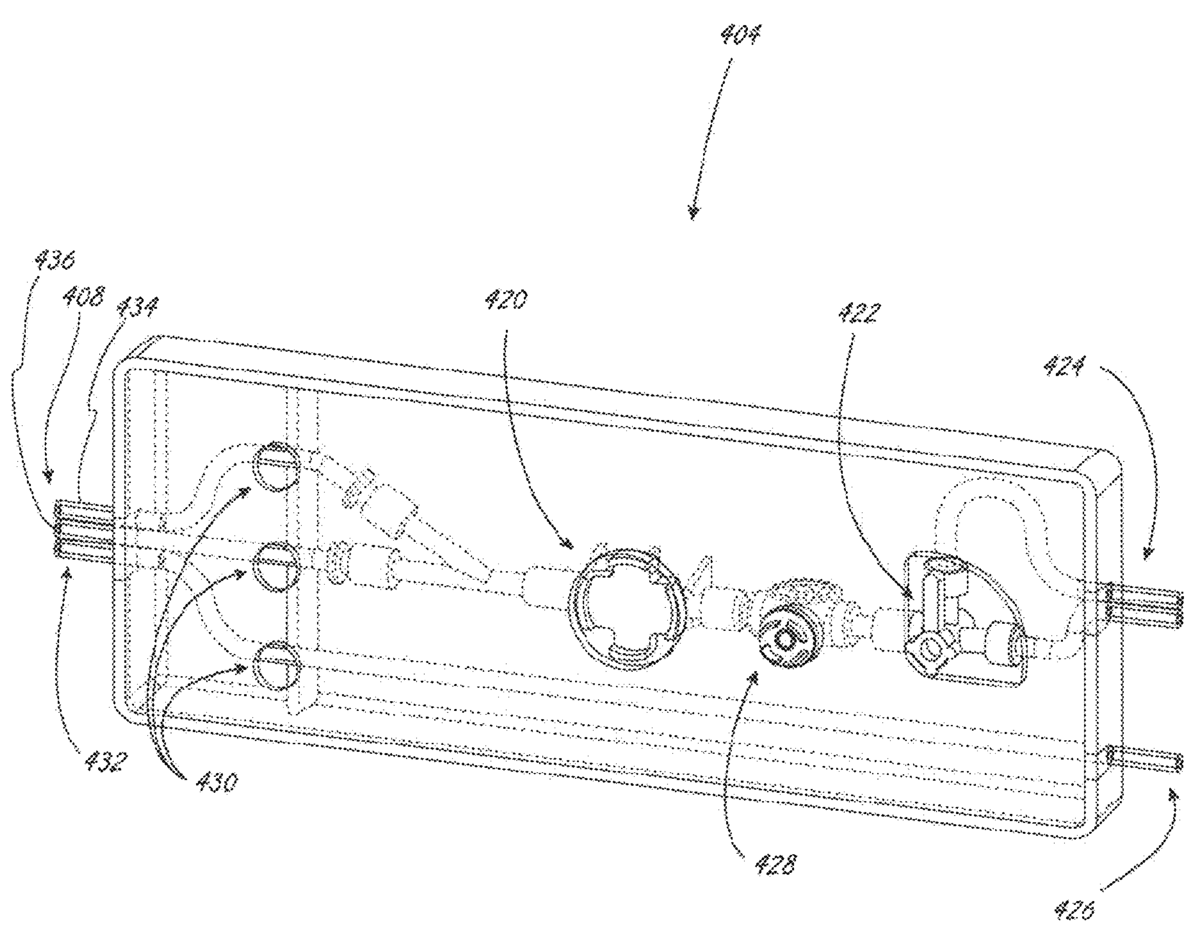
FIG. 9 illustrates a merely exemplary fluid cassette that may be part of any of the external console assemblies herein.

FIG. 9 illustrates a merely exemplary fluid cassette 404, showing a perspective view of an internal or inner side of the cassette that is configured to be inserted into and engaged with an external console, such as console 2610 in FIG. 3. The cassette in this embodiment includes a flow regulator in the form of pump or a portion of pump 428, optional pressure sensor 420, and optional fluid input reservoir regulator 422. The left side of the cassette 404 in the figure illustrates a portion of fluid lines or pathways that extend towards the catheter assembly (not shown) of the intravascular blood pump. In this example, one of the fluid lines may be part of a fluid pathway for waste fluid from the catheter assembly, which may flow to a waste reservoir. Two of the fluid input lines shown extending from the right side of the cassette in the figure reservoirs may receive fluid therethrough from one or more clean purge fluid reservoirs. Cassette 404 includes optional second flow controller or regulator 415 (e.g., a valve, optionally electrically controlled, optionally via feedback) that may be configured to control which fluid reservoir is input to the blood pump (in optional embodiments in which there are more than one clean fluid reservoir). Optional pressure sensor 420 may be a proximal pressure sensor for the system and may be configured to sense fluid pressure in the system at the location of the pressure sensor, although the system may include additionally placed or alternatively placed pressure sensors, which is described in more detail herein. The cassette may optionally (but not necessarily) have openings 430 (or any other kind of aperture) in the internal side surface, which may optionally allow hardware in the console to interface with one or more of the fluid lines shown (e.g., two lines in, one waste out) to optionally contribute to controlling the flow of fluid through one or more of the fluid lines. In the merely exemplary embodiment of FIG. 9, the external console may include one or more valves, such as pinch valves, that are adapted to function as a type of flow regulator or controller to allow flow to be controlled and directed towards or away from the blood pump.

In any of the embodiments herein, the return fluid pathway or line may also include one or more of pressure sensor(s) or flow sensor(s) at any location(s) along the fluid pathway to sense a characteristic of fluid in the line, the sensed information from which may be communicated to a controller in the handle as is described in more detail herein. Any of the sensors herein may be in electrical communication (directly or indirectly) with the blood pump controller. Fluid cable or connect 408 may be connected with the cassette 404 before or after cassette 404 in engaged and secured to the external console.

One of the optionally three catheter assembly input lines shown to the left in FIG. 9 may be in fluid communication with a sheath fluid pathway, and one of the optionally three fluid lines may be considered a clean fluid pathway to the catheter assembly. One of the optionally three lines may be a fluid waste line that may carry return fluid out of the catheter assembly to a waste reservoir.

Optional flow regulator 428 may be, or may be part of, a pulsatile pump to provide flow, and may be driven by a stepper motor in the external console (not shown). The pump may optionally be adapted to operate at one or more fixed speeds, with or without a speed feedback loop. Optional pressure sensor 420 may be configured to detect one or more of fluid pathway blockages, overpressure conditions, or underpressure conditions that may be indicative of a leak in the fluid pathway.

Figure 10:
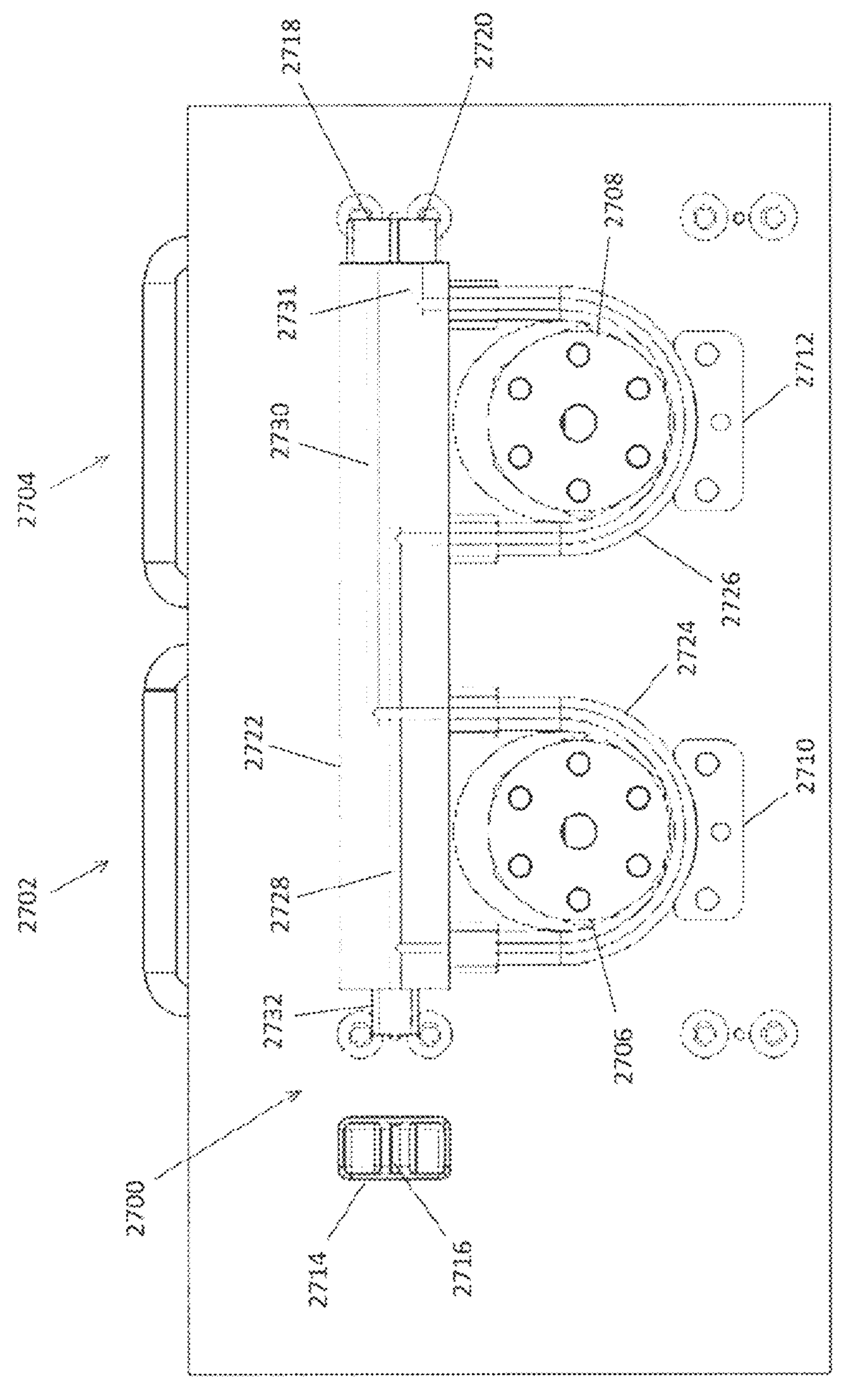
FIG. 10 illustrates a portion of a merely exemplary external console assembly, including portions of optional first and second fluid pathways.

FIG. 10 shows an example of an external console assembly that includes fluid cassette 2700 that is adapted to be mounted to a cassette receiving area of an external console. In this example, the external console assembly includes a first pump 2702 and a second pump 2704. The fluid cassette 2700 may be configured to releasably and operationally coupled with the fluid cassette receiving area 2701 of a console. The first pump 2702 and the second pump 2704 may be peristaltic pumps. In this example, the two-pump configuration can allow for separate and independent control of fluid through a first fluid pathway (e.g., catheter fluid pathway) and a second fluid pathway (e.g., a sheath fluid pathway). Fluid cassette 2700 includes a first fluid line as part of a first fluid pathway (e.g., catheter fluid pathway) and a second fluid line as part of a second fluid pathway (e.g., a sheath fluid pathway). An inlet tubing support 2714 of the cassette receiving area 2701 may be configured to support an inlet tubing from, for example, a clean fluid source 2612 (FIG. 3). Fluid from the clean fluid source is directed to a manifold 2722 via a manifold inlet 2732, which directs the clean fluid to a first flexible tubing 2724 and a second flexible tubing 2726. A first pump head 2706 of the first pump 2702 is configured to operationally engage with and pump fluid through the first flexible tubing 2724. Likewise, a second pump head 2708 of the second pump 2704 is configured to operationally engage with and pump fluid through the second flexible tubing 2726. The clean fluid is pushed back through the manifold 2722 and out of the manifold through a first manifold outlet 2718 and a second manifold outlet 2720, which are connected to corresponding tubing to the catheter. The manifold 2722 includes a manifold inlet channel 2728 that directs fluid from the manifold inlet 2732 to the first flexible tubing 2724 and the second flexible tubing 2726. The manifold 2722 also includes a first manifold outlet channel 2730 that directs fluid from the first flexible tubing 2724 to the first manifold outlet 2718, and a second manifold outlet channel 2731 that directs fluid from the second flexible tubing 2726 to the second manifold outlet 2720. The first manifold outlet 2718 may optionally be connected to tubing that provides fluid communication to a catheter or a sheath, and the second manifold outlet 2720 may optionally be connected to tubing that provides fluid communication to the other of the catheter or the sheath. FIG. 10 is a merely exemplary portion of an exemplary external console assembly that may be adapted to be in fluidic communication with any of the catheter assemblies herein.

FIG. 6 provides exemplary flow and pressure waveforms, one or more aspects of which (e.g., a waveform, an amplitude, a temporal aspect) may be utilized according to any risk mitigation process or system herein. Fluid characteristics herein may be stored in one or more memory units disposed in a blood pump controller, wherein the sensed information may be compared against the stored information. The blood pump controller may be configured to detect, determine, compare, or otherwise indicate (e.g., via an output) if one or more sensed fluid characteristics or information indicative thereof indicates a problem with the external console.

In some exemplary embodiments, a blood pump controller (an example of which is shown in FIG. 2) may have stored therein one or more computer executable methods (e.g., one or more algorithms) that is adapted to compare stored information with sensed information (or information that is indicative of sensed information) to determine if the sensed information is, for example, different than the stored information, outside a range of expected information, above or below a threshold, or simply different than expected information. Any of these situations may be considered to a triggering event herein. In the event of a triggering event herein, the computer executable method may include taking or initiating an action (e.g., providing an output) indicating the triggering event, which may cause or initiate an alert to a user that one or more aspects of the system is not functioning properly.

The risk mitigation benefits herein may include the system performing or taking one or more actions if there is an indication that one or more sensed characteristics of fluid in a fluid path indicate that an aspect of an external console is not functioning properly (i.e., a triggering event). For example, an action may be performed if there is an indication that a fluid flow controller in an external console is not functioning properly, such as a fluid flow controller that is adapted to control or cause fluid flow through one or more fluid pathways herein.

In some embodiments, the action may include an output generated by a process such as an algorithm (e.g., firmware, software, etc.). The action may include providing or causing an alert that can provide an indication that one or more aspects of the external console assembly (e.g., one or more of software, firmware, or hardware) is not functioning properly. For example, a blood pump controller (an example of which is shown in FIG. 2) may provide an output to one or more system components that can initiate and/or provide a notification or alert.

In some embodiments, an alert or notification may be provided by the blood pump. For example, the blood pump may include any number of indicators that are adapted to provide an indication of the detected event. In some exemplary embodiments the blood pump may include any number of visual indicators (e.g., lights, such as LED(s), audible indicators (e.g., a sound such as a beep), and/or tactile indicators (e.g., vibratory) that are adapted to provide or indicate a notification or alert. In some embodiments, the blood pump is adapted to initiate a communication to an external device (e.g., an external console) to provide alert of the detected event. Any communications between the blood pump and the console may be wired or wireless.

The external console may be adapted to provide a notification or alert of the event. For example, an aspect of the console outside of the control of the operating system may be configured to provide a notification of the event, such as any of the indicators herein: visual (e.g., on a display, LED); audio (e.g., a sound), tactile (e.g., vibration), etc.

Figure 7:
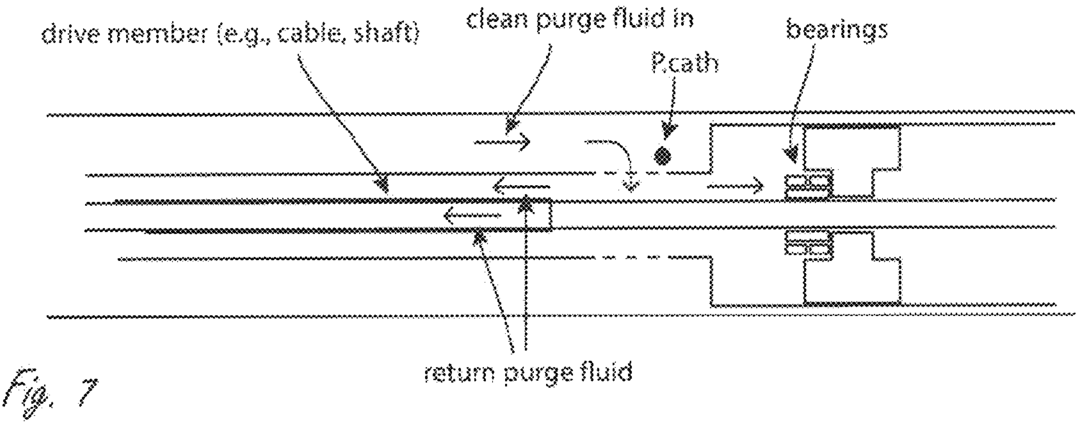
FIG. 7 schematically illustrates a portion of a catheter portion of an exemplary intravascular blood pump, including an optional pressure sensor location in a clean purge fluid pathway.
Figure 8:
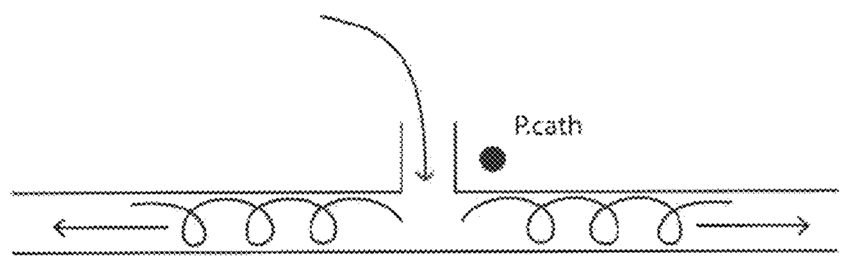
FIG. 8 schematically illustrates a portion of the catheter portion from FIG. 7, including an optional pressure sensor location.

FIG. 7 schematically illustrates a portion of a catheter portion of an exemplary intravascular blood pump, with the distal direction to the right and the proximal direction to the left. The disclosure related to FIG. 7 may be combined with the disclosure related to FIG. 4. FIG. 7 illustrates a portion of a clean purge fluid in pathway, which may be delivered from a clean fluid reservoir using an external console. The fluid pathway, a highlighted region of which is shown in FIG. 8, includes fluid flowing radially inward from the clean purge fluid pathway, after which a portion of the fluid continues to flow distally, as shown, and a portion of which continues to flow proximally toward the external console, as shown. The fluid flowing proximally is shown as return fluid, which flows proximally out of the blood catheter assembly to a waste reservoir.

The blood pump may include one or more pressure sensors that are adapted to sense pressure at one or locations in the intravascular blood pump. For example, a pump portion of the blood pump may include one or more pressure sensors, such as at or adjacent to one or both of an inflow and/or an outflow. One or more pump portion pressure sensors are generally indicated by the pressure sensor on the right in FIG. 5. The system may also include a pressure sensor adjacent and downstream to a pump in the console, such as the pressure sensor shown in FIG. 5 on the left of the figure. The blood pump may also include a pressure sensor as shown in FIGS. 5, 7 and 8, which may be generally disposed in a purge flow path and upstream (relative to a purge flow direction) to the pump portion that includes one or more impellers.

Any of the pressure sensors herein may be in wired communication with a controller, or any of the pressure sensors herein may be in wireless communication with a controller.

In some exemplary implementations, an external console and a catheter assembly may be put into operable communication with each other (e.g., as shown in FIGS. 2 and 3). The stored fluid information herein that is used in the risk mitigation may initially be stored in the external console and/or the information may be stored outside of an external console (e.g., in the blood pump). If the information is initially stored in an external console (e.g., in a software application on the console), the information may be passed to the blood pump controller when they are connected and stored thereon after they have been placed in communication. For example, waveform data (such as that shown in FIG. 6) that may be expected once the blood pump is activated may be communicated to the blood pump and stored thereon. After the blood pump is activated, the controller may then be able to receive sensed information and determine if one or more aspects of the external console are not functioning properly by comparing the sensed information with the expected information. Any of the examples of sensed information and stored information herein may be utilized in this manner. For example, expected timing aspects of fluid flow and/or fluid pressure may be communicated from the console to the blood pump and stored thereon in, for example, a blood pump controller. During operation of the pump portion, the controller may then compare any received sensed information (e.g., related to or indicative of fluid flow and/or fluid pressure) with the stored information, and provide or cause an output that indicates that there is a difference between the expected information and the sensed information. As set forth, the stored information may be information indicative of a wide variety of aspects of flow and/or pressure, and the specific type(s) of information herein are merely exemplary and are not intended to be limiting.

In any of the embodiments herein, the blood pump controller may be adapted to receive and utilize information indicative of both fluid flow and/or fluid pressure. For example, in some merely exemplary embodiments, the controller may receive information indicative of sensed fluid flow and sensed fluid pressure, and compare the information with stored information indicative of flow and pressure, such as without limitation, indicative of one or more of expected amplitude, expected duration of a phase, etc.

Any of the processes or systems herein may include an intravascular blood pump with one or more processes initially stored in a blood pump controller. For example, a blood pump may include a controller with firmware on which one or more process are stored, such as for example without limitation, a timing protocol for hardware control, such as a flow regulator (e.g., a pump, a switch). After the blood pump and external console are put in operable communication, information (e.g., one or more algorithms) may be communicated from the catheter assembly and stored on the external console. The console may then have stored thereon one or more processes to control one or more hardware features on the console (e.g., one or more peristaltic pumps).

In some instances, one or more blood pumps may have different operating conditions stored thereon in one or more memory units. The operating conditions may be stored in the blood pump prior to being put into operable communication with the console, such as when a microcontroller with firmware stored thereon is coupled to electronics of a blood pump. For example, a first blood pump may have operating conditions stored thereon that are different than one or more operating conditions of a second blood pump (or second type of blood pump). Blood pumps with different operating conditions may have one or differences, such as without limitation, number of impellers, expanded diameter size, fluid conduit length, application, etc. Operating conditions that may be different for different blood pumps may include any of, for example without limitation, expected characteristics of flow, expected characteristics of pressure, operating conditions of hardware on an external console (e.g., peristaltic pumps, flow regulator(s)) operating conditions of hardware on the blood pump (e.g., motor). Implementations that include one or more blood pump characteristics stored on the blood pump that are communicated to an external console once coupled together provides for the benefit of being able to communicate any number of protocols or procedures to the external console for any number of blood pumps, and once communicated the console may then be able to control one or more console features in a manner that may be specific to the blood pump, patient, application, setting, etc. For example, there may be several different blood pump models, each of which may have different timing information. Passing (optionally automatically) this information from the blood pump to the console may allow the console to know to which blood pump it is connected/talking to.

Figure 11:
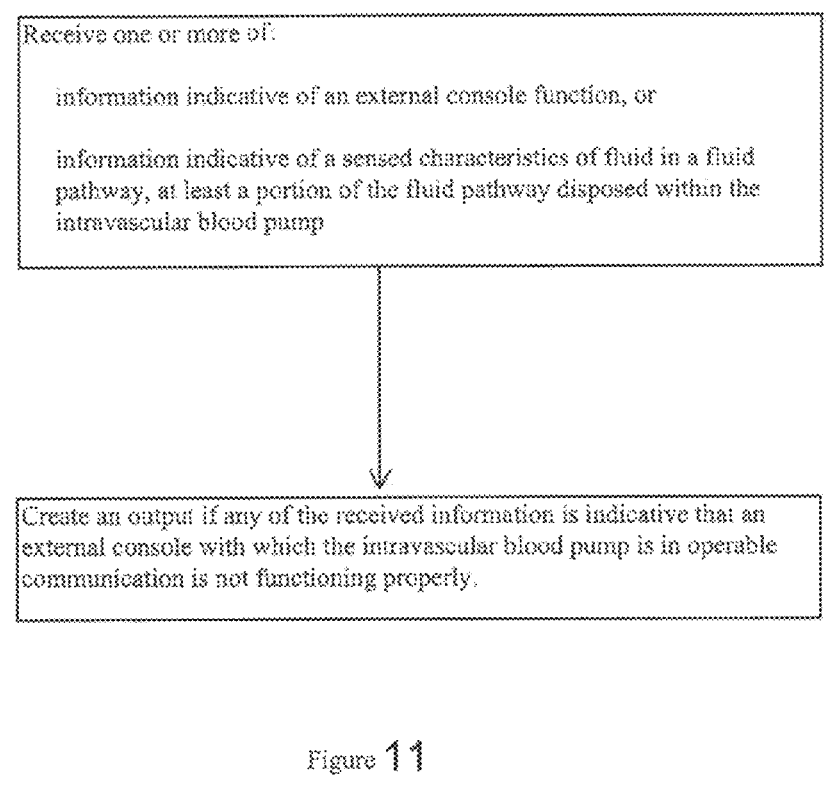

FIG. 11 illustrates an exemplary method, such as a computer executable method, that may be executed by a processor (e.g., microprocessor) and adapted for use with any of the intravascular blood pumps herein. The exemplary method shown in FIG. 10 includes optional first and second steps, although the method may optionally include any other suitable method step herein. FIG. 10 is thus meant to illustrative of computer executable methods herein. Any of the methods herein may thus be represented as a flow diagram as shown in FIG. 10, even if the figure is not expressly included herein in the figure set. Additional method steps may include any suitable step herein, including any steps in one or more of the Detailed Description and Claims.

One optional aspect of the disclosure may be related to preventing blood from entering the catheter and/or contacting the drive assembly. In some implementations the aspect can use the delivery of purge fluid through the blood pump to prevent blood from entering into one or more spaces in the blood pump (other than through the fluid conduit, through which blood is pumped). That is, purge fluid can be pumped through and out of the catheter to prevent blood from entering into one or more purge fluid paths. In some illustrative examples, the pump portion includes one or more pressure sensors (e.g., one or both of an inflow and outflow sensors), schematically illustrated in FIG. 5 as the "pressure sensor" on the right side of the figure. There may be a sensor in the catheter disposed to sense pressure along an inflow purge fluid path, such as where the central "pressure sensor" is shown in FIG. 5. This exemplary pressure sensor location is also shown in FIGS. 7 and 8. One way of preventing blood from flowing into the purge fluid pathway in the blood pump may be to make sure the pressure in the catheter (e.g., P.cath) is at least the same as and more likely greater than the pressure at the pump portion. Generally speaking, this ensure the pressure along the purge fluid pathway in the catheter is greater than pressure in the purge fluid pathway at the pump, making surge purge fluid is pumped at a rate/pressure to make sure it flows and prevents blood from coming into the catheter. The system can include one or more processes stored thereon that are adapted to receive sensed pressure information and control the delivery of purge fluid to maintain P.cath at least the same as and generally greater than pressure at the pump portion (which may also be referred to herein as pressure at the patient (blood pressure)).

In any of the embodiments herein, a flow regulator in the console may be any type of suitable flow regulator. In FIG. 5, the flow regulator is shown as an optional switch, which may be a binary switch (open/closed), but which may be a variable switch, to allow for finer control of return purge fluid flow characteristics. An external flow regulator may also be a pump, such as a peristaltic pump or a portion of a peristaltic pump.

The disclosure herein describes exemplary systems in which a blood pump may receive sensed information and may utilize that in risk mitigation processes. In some more generalized implementations, a blood pump may expect to receive information from an external console, and if that information is not received, it may indicate that one or more functions of the console are not functioning properly. For example, a blood pump controller may be adapted to expect a periodic signal/communication from an external console. If the controller does not receive the signal/communication as or when expected, the controller may then provide an output (such as any of those herein) that causes any number of actions to take place that indicate the discrepancy.

Even if not specifically indicated, one or more techniques described in this disclosure may be implemented, at least in part, in hardware, software, firmware or any combination thereof. For example, various aspects of the techniques or components may be implemented within one or more processors, including one or more microprocessors, digital signal processors (DSPs), application specific integrated circuits (ASICs), field programmable gate arrays (FPGAs), programmable logic circuitry, or the like, either alone or in any suitable combination. The term "processor," "controller," "control unit," or derivatives thereof may generally refer to any of the foregoing circuitry, alone or in combination with other circuitry, or any other equivalent circuitry.

Such hardware, software, or firmware may be implemented within the same device or within separate devices to support various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, functionality ascribed to systems, devices and techniques described in this disclosure may be embodied as instructions on a computer-readable medium such as random access memory (RAM), read only memory (ROM), non-volatile RAM (NVRAM), electrically erasable programmable ROM (EEPROM), Flash memory, and the like. The instructions may be executed by a processor to support one or more aspects of functionality described in this disclosure.

The Detailed Description includes an Appendix section. Any suitable aspect of the Detailed Description included in either the Appendix portion or the non-Appendix portion may be incorporated with aspects of the other portion of the Detailed Description, including without limitation devices, components, parts, portions, and method steps including methods of deployment and use. For example, any of the exemplary pump portions in the Appendix section may also include any suitable aspect described in the non-Appendix portion, such as, without limitation, methods executable by a processor. Reference numbers or figures in the non-Appendix portion of the Detailed Description figures, even if they are duplicative of reference numbers or figures in the Appendix section, are understood to apply to the non-Appendix section of the Detailed Description.

The invention claimed is:

1. An intravascular blood pump system, comprising:

a catheter assembly including, a handle portion sized and configured to be held by a user, a catheter portion extending distally from the handle portion, a pump portion disposed at a distal end of the catheter portion, and a fluid pathway disposed within the catheter portion;

and an external console assembly, the catheter assembly and the external console assembly adapted and configured to be put into fluidic communication, the handle portion comprising a controller configured to access stored information pertaining to one or more expected operational parameters within the external console assembly, the controller being configured to receive sensed information that is indicative of a sensed characteristic of fluid in the fluid pathway, the controller being configured to perform a comparison between the sensed information and the stored information, and the controller being configured to cause an alert when the comparison is indicative that the external console assembly is not functioning properly.

2. The system of claim 1, further comprising a pressure sensor disposed in the fluid pathway, the sensed characteristic indicative of fluid pressure in the fluid pathway.

3. The system of claim 2, wherein the pressure sensor is disposed within the external console assembly.

4. The system of claim 2, wherein the pressure sensor is disposed within the catheter assembly.

5. The system of claim 4, wherein the pressure sensor is disposed within the handle portion.

6. The system of claim 4, wherein the pressure sensor is disposed within the catheter portion.

7. The system of claim 1, wherein the fluid pathway is a clean purge fluid pathway.

8. The system of claim 1, wherein the fluid pathway is a return fluid pathway.

9. The system of claim 1, wherein the fluid pathway is a sheath fluid pathway that includes a section disposed between an outer axially movable sheath and an outer surface of an inner catheter shaft.

10. The system of claim 1, further comprising a fluid pump in the external console assembly, the fluid pump adapted and positioned to pump fluid in the fluid pathway.

11. The system of claim 10, wherein the fluid pump is adapted and positioned to pump fluid in a clean purge fluid pathway.

12. The system of claim 10, wherein the catheter portion further comprises a catheter shaft having an outer surface, an outer sheath disposed over the catheter shaft. and a sheath fluid pathway formed between the outer surface of the catheter shaft and the outer sheath, wherein the fluid pump is adapted and positioned to pump fluid in the sheath fluid pathway.

13. The system of claim 1, wherein the sensed information is indicative of a sensed fluid pressure amplitude of fluid in the fluid pathway.

14. The system of claim 1, wherein the sensed information is indicative of a sensed fluid pressure waveform over time of fluid in the fluid pathway.

15. The system of claim 1, wherein the handle portion comprises an indicator that is adapted to communicate the alert.

16. The system of claim 1, wherein the external console assembly comprises an indicator that is adapted to communicate the alert.

17. The system of claim 1, wherein the stored information is an expected sensed pressure amplitude within the external console assembly.

18. The system of claim 1, wherein the stored information is an expected pressure waveform over time within the external console assembly.

19. The system of claim 1, wherein the comparison is indicative of the external console assembly operating outside of an expected fluid pressure range.

20. The system of claim 1, wherein the external console assembly comprises an operating system adapted to be in direct or indirect control of one or more fluid pumps in the external console assembly, one of the one or more pumps positioned and adapted to pump fluid in the pathway.

* * * * *